(12) United States Patent
Jakobsen et al.

(10) Patent No.: US 7,425,339 B2
(45) Date of Patent: Sep. 16, 2008

(54) CD8ALPHA MUTANTS

(75) Inventors: Bent Karsten Jakobsen, Oxfordshire (GB); Meir Glick, Stoughton, MA (US)

(73) Assignee: MediGene Limited, Oxfordshire (GB)

( * ) Notice: Subject to any disclaimer, the term of this patent is extended or adjusted under 35 U.S.C. 154(b) by 461 days.

(21) Appl. No.: 10/479,509

(22) PCT Filed: Jun. 14, 2002

(86) PCT No.: PCT/GB02/02743

§ 371 (c)(1),
(2), (4) Date: Dec. 10, 2003

(87) PCT Pub. No.: WO02/102852

PCT Pub. Date: Dec. 27, 2002

(65) Prior Publication Data

US 2004/0157288 A1 Aug. 12, 2004

(30) Foreign Application Priority Data

Jun. 14, 2001 (GB) .................. 0114533.3

(51) Int. Cl.
*A61K 38/17* (2006.01)
*C07K 14/725* (2006.01)

(52) U.S. Cl. .................. 424/278.1; 514/2; 514/885; 530/350; 530/868

(58) Field of Classification Search .................. None
See application file for complete search history.

(56) References Cited

FOREIGN PATENT DOCUMENTS

WO     WO 99 21576 A    5/1999

OTHER PUBLICATIONS

Gao, et al, "Molecular Interactions of Coreceptor CD8 and MHC Class I: the molecular basis for functional coordination with the T-cell receptor", Immunology Today, Dec. 1, 2000, pp. 630-636, vol. 21, No. 12, Elsevier Publications, GB.
Sewell et al., "Antagonism of Cytotoxic—T-lymphocyte Activation by Soluble CD8," Nature Medicine, Apr. 1999, pp. 399-404, vol. 5, No. 4, Nature Medicine, USA.
Kern, et al., "Structural Basis of CD8 Coreceptor Function Revealed by Crystallographic Analysis of a Murine CD8 Alphaalpha Ectodomain Fragment in Complex with H-2Kb," Immunity, Oct. 1998, pp. 519-530, vol. 9, No. 4, Cell Press, USA.
Li et al., "Identification of the CD8 DE Loop as a Surface Functional Epitope. Implications for Major Histocompatibility Complex Class I Binding and CD8 Inhibitor Design," The Journal of Biological Chemistry, Jun. 26, 1998, pp. 16442-16445, vol. 273, No. 26, Amer. Soc. For Biochem. And Mol. Bio., Inc., USA.
Giblin et al., "A secreted form of the human lymphocyte cell surface molecule CD8 arises from alternative splicing," *Proc. Natl. Acad. Sci. USA 86*, 998-1002, Feb. 1989.

*Primary Examiner*—Ron Schwadron
(74) *Attorney, Agent, or Firm*—Banner & Witcoff, Ltd.

(57) ABSTRACT

The present invention provides modified CD8 molecules whose binding to MHC is enhanced compared to wild-type CD8, wherein $Ser_{53}$ of at least one CD8α chain thereof is mutated to another amino acid. It also provides nucleic acids encoding such molecules and methods of using such molecules and nucleic acids in immunosuppressive therapy, in particular as inhibitors of cytotoxic T cell responses.

6 Claims, 8 Drawing Sheets

Figure 1a

```
-21                              -10
 M   A   L   P   V   T   A   L   L   P   L   A   L   L   L   H   A   A   R
atggccttaccagtgaccgccttgctcctgccgctggccttgctgctccacgccgccagg -1  1                            10
 P   S   Q   F   R   V   S   P   L   D   R   T   W   N   L   G   E   T   V   E
ccgagccagttccgggtgtcgccgctggatcggacctggaacctgggcgagacagtggag 20                               30
 L   K   C   Q   V   L   L   S   N   P   T   S   G   C   S   W   L   F   Q   P
ctgaagtgccaggtgctgctgtccaacccgacgtcgggctgctcgtggctcttccagccg 40                               50
 R   G   A   A   A   S   P   T   F   L   L   Y   L   S   Q   N   K   P   K   A
cgcggcgccgccgccagtcccaccttcctcctatacctctcccaaaacaagcccaaggcg 60                               70
 A   E   G   L   D   T   Q   R   F   S   G   K   R   L   G   D   T   F   V   L
gccgagggcctggacacccagcggttctcgggcaagaggttgggggacaccttcgtcctc 80                               90
 T   L   S   D   F   R   R   E   N   E   G   Y   Y   F   C   S   A   L   S   N
accctgagcgacttccgccgagagaacgagggctactatttctgctcggccctgagcaac 100                              110         115
 S   I   M   Y   F   S   H   F   V   P   V   F   L   P   A   K   P   T   T   T
tccatcatgtacttcagccacttcgtgccggtcttcctgccagcgaagcccaccacgacg 120                              130
 P   A   P   R   P   P   T   P   A   P   T   I   A   S   Q   P   L   S   L   R
ccagcgccgcgaccaccaacaccggcgcccaccatcgcgtcgcagcccctgtccctgcgc 140                              150
 P   E   A   C   R   P   A   A   G   G   A   V   H   T   R   G   L   D   F   A
ccagaggcgtgccggccagcggcggggggcgcagtgcacacgagggggctggacttcgcc 160                              170
 C   D   I   Y   I   W   A   P   L   A   G   T   C   G   V   L   L   L   S   L
tgtgatatctacatctgggcgcccttggccgggacttgtggggtccttctcctgtcactg 180                   188   190
 V   I   T   L   Y   C   N   H   R   N   R   R   R   V   C   K   C   P   R   P
gttatcacccttactgcaaccacaggaaccgaagacgtgtttgcaaatgtccccggcct 200                              210
 V   V   K   S   G   D   K   P   S   L   S   A   R   Y   V   *
gtggtcaaatcgggagacaagcccagcctttcggcgagatacgtctaa
```

Figure 1b

```
<----------------- Immunoglobulin like domain --------
  S   Q   F   R   V   S   P   L   D   R   T   W   N   L   G   E   T   V   E
AGtCAaTTtCGtGTaTCaCCGCTGGATCGGACCTGGAACCTGGGCGAGACAGTGGAG -------------------------------------------------------------
  L   K   C   Q   V   L   L   S   N   P   T   S   G   C   S   W   L   F   Q   P
CTGAAGTGCCAGGTGCTGCTGTCCAACCCGACGTCGGGCTGCTCGTGGCTCTTCCAGCCG -------------------------------------------------------------
  R   G   A   A   A   S   P   T   F   L   L   Y   L   N   Q   N   K   P   K   A
CGCGGCGCCGCCGCCAGTCCCACCTTCCTCCTATACCTCAACCAAAACAAGCCCAAGGCG -------------------------------------------------------------
  A   E   G   L   D   T   Q   R   F   S   G   K   R   L   G   D   T   F   V   L
GCCGAGGGGCTGGACACCCAGCGGTTCTCGGGCAAGAGGTTGGGGGACACCTTCGTCCTC -------------------------------------------------------------
  T   L   S   D   F   R   R   E   N   E   G   Y   Y   F   C   S   A   L   S   N
ACCCTGAGCGACTTCCGCCGAGAGAACGAGGGCTACTATTTCTGCTCGGCCCTGAGCAAC -----------------------------------------------> <Membrane p.d.
  S   I   M   Y   F   S   H   F   V   P   V   F   L   P   A   K   P   T   T   T
TCCATCATGTACTTCAGCCACTTCGTGCCGGTCTTCCTGCCAGCGAAGCCCACCACGACG

--
  P   *
CCATAG
```

Figure 1c

```
-21                              -10
  M  A  L  P  V  T  A  L  L  L  P  L  A  L  L  L  H  A  A  R
 atggccttaccagtgaccgccttgctcctgccgctggccttgctgctccacgccgcagg -1  1                                10
  P  S  Q  F  R  V  S  P  L  D  R  T  W  N  L  G  E  T  V  E
 ccgagccagttccgggtgtcgccgctggatcggacctggaacctgggcgagacagtggag 20                               30
  L  K  C  Q  V  L  L  S  N  P  T  S  G  C  S  W  L  F  Q  P
 ctgaagtgccaggtgctgctgtccaacccgacgtcgggctgctcgtggctcttccagccg 40                               50
  R  G  A  A  A  S  P  T  F  L  L  Y  L  N  Q  N  K  P  K  A
 cgcggcgccgccgccagtcccaccttcctcctatacctcaaccaaaacaagcccaaggcg 60                               70
  A  E  G  L  D  T  Q  R  F  S  G  K  R  L  G  D  T  F  V  L
 gccgaggggctggacacccagcggttctcgggcaagaggttgggggacaccttcgtcctc 80                               90
  T  L  S  D  F  R  R  E  N  E  G  Y  Y  F  C  S  A  L  S  N
 accctgagcgacttccgccgagagaacgagggctactatttctgctcggccctgagcaac 100                             110        115
  S  I  M  Y  F  S  H  F  V  P  V  F  L  P  A  K  P  T  T  T
 tccatcatgtacttcagccacttcgtgccggtcttcctgccagcgaagcccaccacgacg 120                              130
  P  A  P  R  P  P  T  P  A  P  T  I  A  S  Q  P  L  S  L  R
 ccagcgccgcgaccaccaacaccggcgcccaccatcgcgtcgcagcccctgtccctgcgc 140                              150
  P  E  A  C  R  P  A  A  G  G  A  V  H  T  R  G  L  D  F  A
 ccagaggcgtgccggccagcggcggggggcgcagtgcacacgaggggctggacttcgcc 160                              170
  C  D  I  Y  I  W  A  P  L  A  G  T  C  G  V  L  L  L  S  L
 tgtgatatctacatctgggcgcccttggccgggacttgtggggtccttctcctgtcactg 180                      188    190
  V  I  T  L  Y  C  N  H  R  N  R  R  R  V  C  K  C  P  R  P
 gttatcacccttactgcaaccacaggaaccgaagacgtgtttgcaaatgtccccggcct 200                              210
  V  V  K  S  G  D  K  P  S  L  S  A  R  Y  V  *
 gtggtcaaatcgggagacaagcccagcctttcggcgagatacgtctaa
```

Figure 1d

```
 L   Q   Q   T   P   A   Y   I   K   V   Q   T   N·
CTC CAG CAG ACC CCT GCA TAC ATA AAG GTG CAA ACC AAC

K   M   V   M   L   S   C   E   A   K   I   S   L
AAG ATG GTG ATG CTG TCC TGC GAG GCT AAA ATC TCC CTC

S   N   M   R   I   Y   W   L   R   Q   R   Q   A
AGT AAC ATG CGC ATC TAC TGG CTG AGA CAG CGC CAG GCA

P   S   S   D   S   H   H   E   F   L   A   L   W
CCG AGC AGT GAC AGT CAC CAC GAG TTC CTG GCC CTC TGG

D   S   A   K   G   T   I   H   G   E   E   V   E
GAT TCC GCA AAA GGG ACT ATC CAC GGT GAA GAG GTG GAA

Q   E   K   I   A   V   F   R   D   A   S   R   F
CAG GAG AAG ATA GCT GTG TTT CGG GAT GCA AGC CGG TTC

I   L   N   L   T   S   V   K   P   E   D   S   G
ATT CTC AAT CTC ACA AGC GTG AAG CCG GAA GAC AGT GGC

I   Y   F   C   M   I   V   G   S   P   E   L   T
ATC TAC TTC TGC ATG ATC GTC GGG AGC CCC GAG CTG ACC

F   G   K   G   T   Q   L   S   V   V   D   *
TTC GGG AAG GGA ACT CAG CTG AGT GTG GTT GAT TAA
```

Figure 2
A: Tax HLA-A2 hCD8aa WT binding: Kd=123.7μM
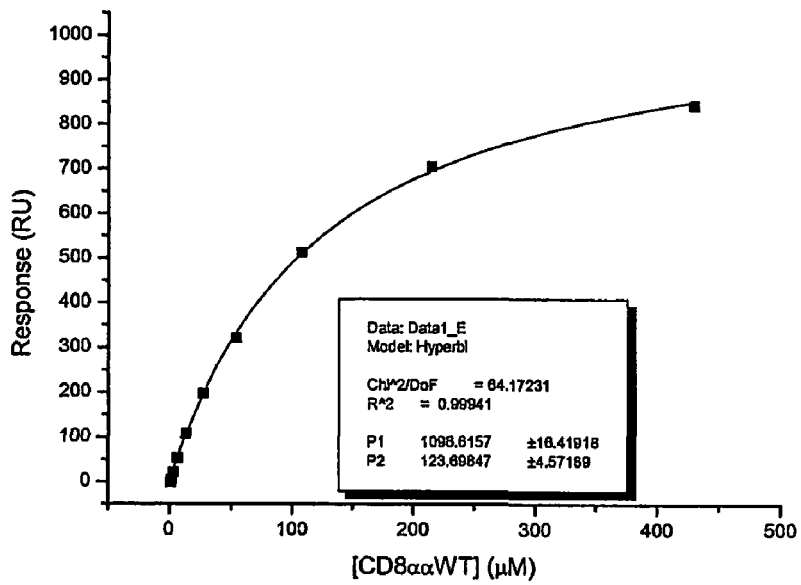
B: Tax HLA-A2 hCD8aa mutant S53→N binding: Kd=35.3μM
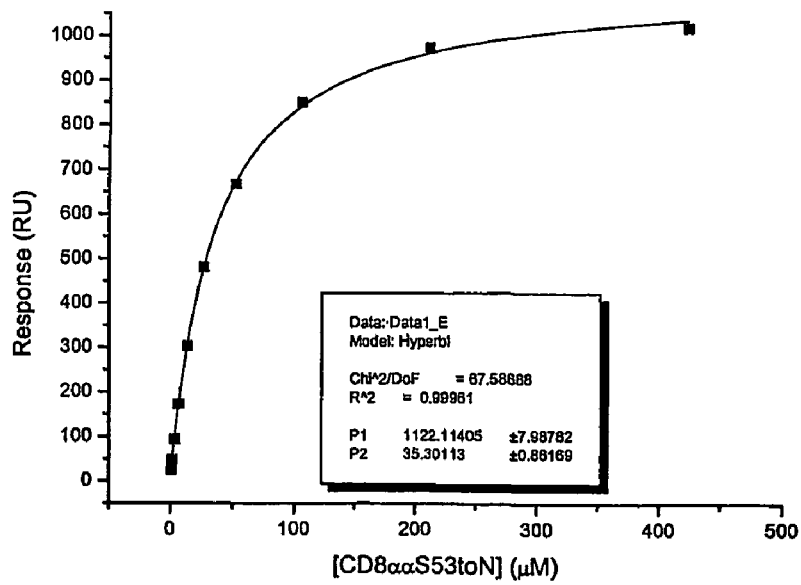

Figure 2
C: Tax HLA-A2 hCD8aa WT binding: Kd=118.7μM
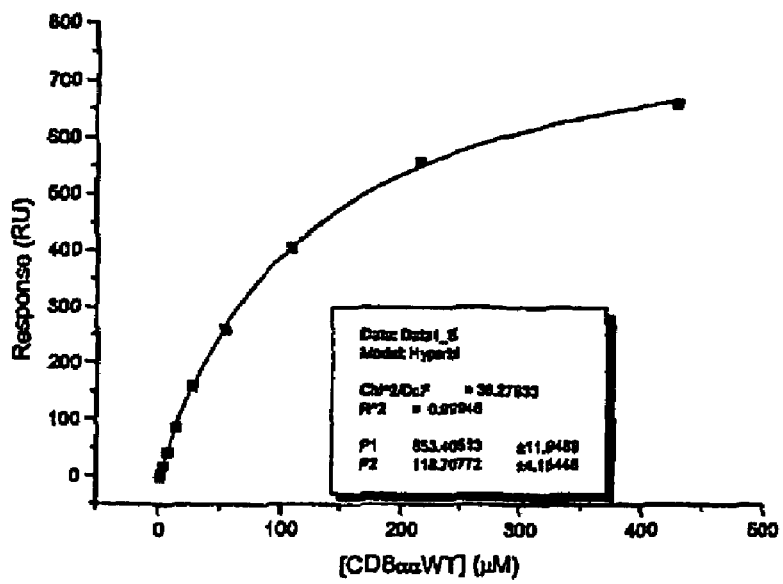
D: Tax HLA-A2 hCD8aa mutant S53→N binding: Kd=34.6μM
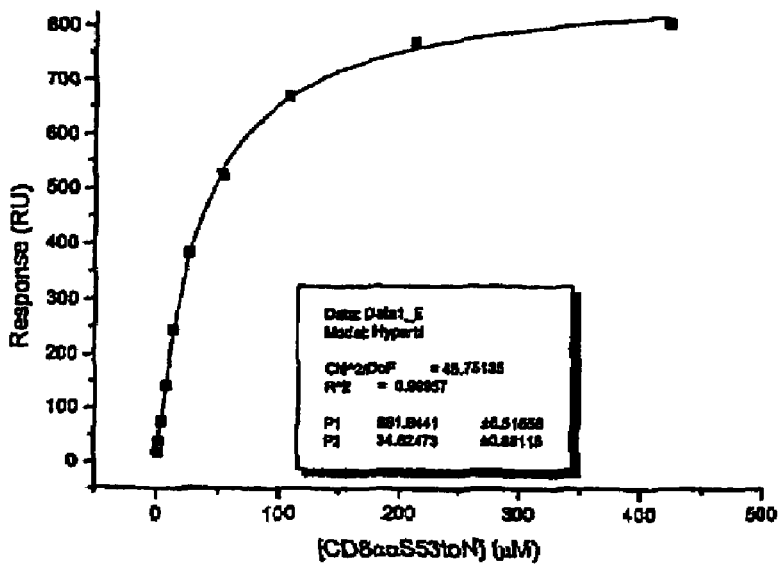

Figure 3
A: Flu HLA-A2 hCD8aa WT binding: Kd=151.7μM
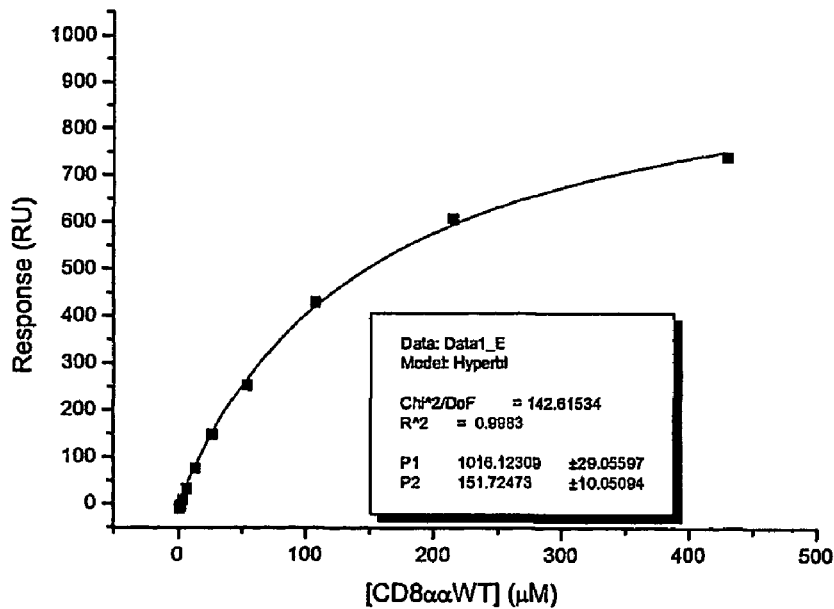
B: Flu HLA-A2 hCD8aa mutant S53→N binding: Kd=50.1μM
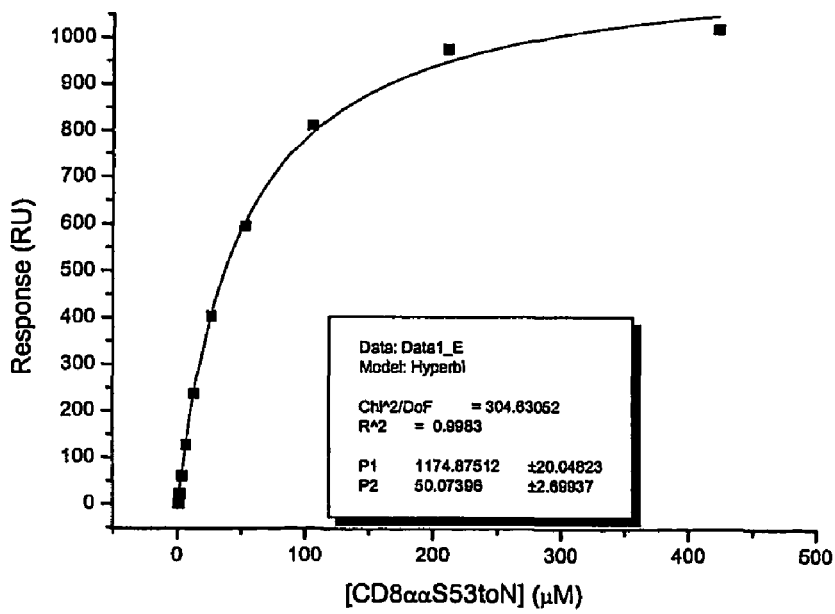

Figure 4
A: Tax HLA-A2 hCD8aa mutant Gln$_2$ → Lys binding: Kd = 363 µM
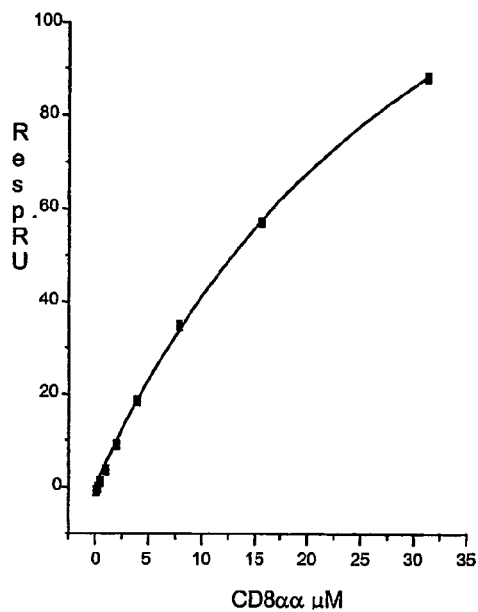
B: Tax HLA-A2 hCD8aa mutant Leu$_{97}$ → Tyr binding: Kd = 630 µM
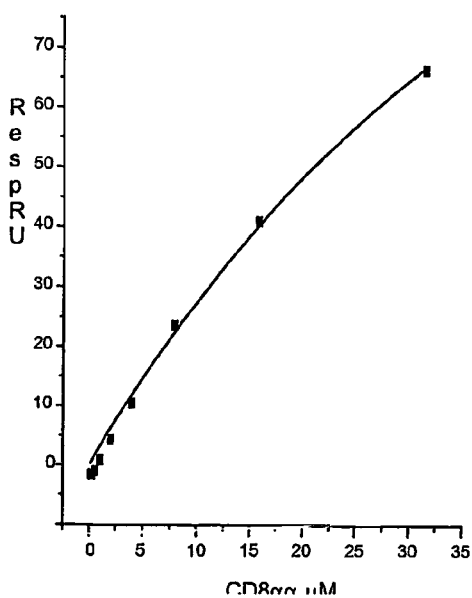

CD8ALPHA MUTANTS

CROSS REFERENCE TO RELATED APPLICATIONS

This application is based upon and claims the benefit of priority from the prior British Patent Application No. 0114533.3, filed Jun. 14, 2001, the entire contents of which are incorporated herein by reference.

The present invention relates to modified CD8 proteins and nucleic acids encoding such proteins, and to their use in immunosuppressive therapy, in particular as inhibitors of cytotoxic T cell responses.

Major histocompatibility complex Class I and II proteins (MHC, or HLA in man) bind peptide antigens and present them on the cell surface. MHC Class I molecules are expressed to varying degrees on most nucleated cells, while Class II expression is restricted to a subset of cells referred to as specialised antigen presenting cells (APCs). Class I molecules present peptides derived from proteins expressed within the cell. Their role is to provide "markers" on the surface of cells to allow the immune system to monitor the state of these cells for abnormalities. Class II molecules obtain peptides derived from proteins taken up by the APCs from the extracellular space. Their role can be considered to be to monitor the extracellular body fluids for foreign antigens. APCs include the interdigitating dendritic cells found in the T cell areas of the lymph nodes and spleen; Langerhan's cells in the skin; follicular dendritic cells in B cell areas of the lymphoid tissue; monocytes, macrophages and other cells of the monocyte/macrophage lineage; B cells and T cells; and a variety of other cells such as endothelial cells and fibroblasts which are not classical APCs but can act in the manner of an APC.

MHC-peptide complexes are recognised by T lymphocytes expressing a unique T cell receptor (TCR) matching the specific MHC-peptide combination. T cell precursors enter the thymus where they undergo a selection procedure ensuring that T cells which respond to self-peptides are eradicated (negative selection). In addition, T cells that do not have the ability to recognise the MHC variants presented, fail to mature (positive selection).

Recognition of specific MHC-peptide complexes by T cells is mediated by the T cell receptor (TCR), which consists of an α and a β chain, both of which are anchored in the membrane. In a recombination process similar to that observed for antibody genes, the TCR α and β genes rearrange from Variable, Joining, Diversity and Constant elements, creating enormous diversity in the extracellular antigen binding domains ($10^{13}$ to $10^{15}$ different possibilities). Antibody receptors and TCRs are the only types of molecules that recognise antigens in a specific manner. The TCR is the only receptor specific for particular peptide antigens presented in MHC, where the peptide is often the only sign of an abnormality within a cell.

CD8 and CD4 are transmembrane glycoproteins characteristic of distinct populations of T lymphocytes whose antigen responses are restricted by class I and class II MHC molecules, respectively. They play major roles both in the differentiation and selection of T cells during thymic development and in the activation of mature T lymphocytes in response to antigen presenting cells. CD8 and CD4 are therefore considered to be the main accessory molecules for T cell receptors and hence are referred to as co-receptors. Mature T cells expressing CD4 are referred to as helper T cells while $CD8^+$ T cells are called killer T cells or cytotoxic T lymphocytes (CTLs). In addition to its role in the positive selection of T cells during differentiation in the thymus, CD8 is essential for the ability of most mature CTLs to kill target cells.

Both CD8 and CD4 are immunoglobulin superfamily proteins. They determine antigen restriction by binding to MHC molecules at an interface distinct from the region presenting the antigenic peptide, but the structural basis for their similar functions appears to be very different. Their sequence similarity is low and, whereas CD4 is expressed on the cell surface as a monomer, CD8 is expressed as an αα homodimer or an αβ heterodimer. CD8 contacts an acidic loop in the α3 domain of Class I MHC, thereby increasing the avidity of the T cell for its target. CD8 is also involved in the phosphorylation events leading to CTL activation through the association of its α chain cytoplasmic tail with the tyrosine kinase $p56^{lck}$.

Suppressors of the cellular arm of the immune system, such as suppressors of CD4 or CD8 T cells, are urgently needed for the treatment of auto-immune disorders, such as rheumatoid arthritis, lupus erthymatosus, psoriasis vulgaris, ankylosing spondylitis, Reiter's disease, post-salmonella arthritis, post-shigella arthritis, post-yersinia arthritis, post-gonococcal arthritis, uveitis, amylodosis, idiopathic hemachromatosis and myasthenia gravis, as well as of hypersensitivity (such as allergic reactions) and the prevention of graft rejection and graft-versus-host disease.

The therapeutic action of antibodies directed against CD4 and CD8 has been assessed (De Fazio, et al. *Transplantation* 61: 104-10 (1996)), but with limited success and antibodies in general are not well suited as drugs since they tend to induce secondary immune responses and are short-lived. Administration of steroids is another way of suppressing the immune system but their effect is extremely indirect and associated with severe side-effects.

It is known that soluble CD8 and derivatives thereof can cause inhibition of CTL. For example, Choksi, et at. (*Nature Medicine* 4: 309-314 (1998)) used free CD8-derived peptides to inhibit CTL. One peptide in particular, "CSSHNKPC" (SEQ ID NO:1), could inhibit both the differentiation and effector stages of CTL response. However, a very high concentration of peptide (>100 μg/ml) was required to bring about this inhibition (>50%). Soluble CD8 has also been shown to cause inhibition of CTL (WO 99/21576; Sewell, et at. *Nature Medicine* 5: 399-404 (1999)). The inhibitory effect of the soluble CD8 molecule was more dramatic than that observed with an anti-CD8 monoclonal antibody.

Although these soluble CD8 molecules can prevent or inhibit $CD8^+$ T cell responses, they have a relatively low affinity for MHC/peptide complex. It is desirable to provide modified CD8-derived peptides and polypeptides which have a higher affinity for MHC so as to enhance the CTL inhibitory effect of soluble CD8.

According to a first aspect of the present invention, there is provided a modified CD8 molecule whose binding to MHC is enhanced compared to wild type CD8, wherein $Ser_{53}$ of at least one CD8α chain thereof is mutated to another amino acid.

According to a second aspect, the present invention provides a nucleic acid, particularly a DNA, comprising a sequence which encodes a modified CD8 molecule whose binding to MHC is enhanced compared to wild type CD8, wherein $Ser_{53}$ is of at least one CD8α chain thereof is mutated to another amino acid.

In a third aspect, the invention provides a composition comprising a modified CD8 molecule of the first aspect or a nucleic acid of the second aspect together with a pharmaceutically acceptable diluent, excipient or carrier.

In a fourth aspect, the invention provides a modified CD8 molecule of the first aspect, or a nucleic acid of the second aspect, for use in medicine.

In a fifth aspect, the invention provides the use of a modified CD8 molecule of the first aspect, or of a nucleic acid of the second aspect, in the manufacture of a medicament for modulating CD8+ T cell response.

In a sixth aspect, the invention provides a method of modulating the activation of a CD8+ T cell by a class I Major Histocompatibility Complex (MHC), the method comprising exposing the class I MHC to a modified CD8 molecule of the first aspect. Nucleic acids of the present invention may be used to transfect cells to produce modified CD8 molecules of the invention in vivo to modulate the activation of a CD8+T cell.

In a seventh aspect, the invention provides a method for the treatment of an autoimmune disorder, hypersensitivity (e.g. allergic reaction), graft versus host disease or graft rejection, comprising administering to a patient a modified CD8 molecule of the first aspect or a nucleic acid of the second aspect.

In an eighth aspect, the present invention provides a product containing a modified CD8 molecule of the first aspect or a nucleic acid of the second aspect and an immunosuppressive agent as a combined preparation for simultaneous, sequential or separate use in modulating CD8+ T cell response.

The present invention is described in more detail herein with reference to the accompanying drawings, in which:

BRIEF DESCRIPTION OF THE DRAWINGS

FIG. 1a shows the amino acid (SEQ ID NO:2) and nucleic acid (SEQ ID NO:3) sequence of the wild-type human CD8α chain, FIGS. 1b and 1c show the amino acid (SEQ ID NO:4, SEQ ID NO:6 and nucleic acid (SEQ ID NO:5, SEQ ID NO:7) sequences of respective soluble and membrane-bound CD8α molecules of the present invention, and FIG. 1d shows the amino acid (SEQ ID NO:8) and nucleic acid (SEQ ID NO:9) sequences of a soluble form of the human CD8β monomer.

FIGS. 2a and c are graphs illustrating the affinity of wild type human CD8αα for Tax/HLA-A2/β2m complex, and FIGS. 2b and d are graphs illustrating the affinity of modified human CD8αα in which $Ser_{53}$ is modified to Asn for Tax/LA-A2/β2m complex;

FIG. 3a is a graph illustrating the affinity of wild type human CD8αα for Flu/HLA-A2/β2m complex, and FIG. 3b is a graph illustrating the affinity of modified human CD8αα in which $Ser_{53}$ is modified to Asn for Flu/HLA-A2/β2m complex; and FIG. 4a is a graph illustrating the affinity of modified human CD8αα in which $Gln_2$ is modified to Lys for Tax/HLA-A2/β2m complex, and FIG. 4b is a graph illustrating the affinity of modified human CD8αα in which $Leu_{97}$ is modified to Tyr for Tax/HLA-A2/β2m complex.

In the present invention, reference to numbered amino acid residues in human CD8 is in accordance with the numbering of the amino acid residues in FIG. 1a.

The modified CD8 molecules of the present invention provide an improvement over those disclosed previously due to their greater ability to occupy the MHC binding site and inhibit CD8+ T cell response. In W0 99/21576, we suggested that knowledge of the molecular structure of CD8αα and a MHC molecule (HLA-A2) meant that it would be possible to design CD8 mutants which have increased binding to MHC, and suggested certain mutations which may have this effect. Surprisingly, we have now found that none of the suggested mutants has increased binding. Indeed, unexpectedly, we have found that of all of the potential mutations available, only mutations of a single amino acid residue have this effect.

In one embodiment, $Ser_{53}$ is mutated to Asn. However, it will be appreciated that $Ser_{53}$ may be mutated to other amino acids, particularly those with similar steric/electrostatic/polar properties to Asn. For example, $Ser_{53}$ may be mutated to Gln or His to create an additional hydrogen bond between CD8 and HLA in the same way as Asn. Alternatively, $Ser_{53}$ may be mutated to Lys. This residue has an electrostatic attraction to $Asp_{227}$ of HLA.

It is preferred if the modified CD8 of the present invention is derived from human CD8. The sequences for two human forms of the CD8 receptor, αα and αβ, are known (EMBL/GENBANK database accession numbers:CD8α, M27161; CD8β, X13444). The two forms of the receptor are functionally equivalent and no significant differences in the effects of using one or the other for immune inhibition would be expected.

The human CD8 gene expresses a protein of 235 amino acids. The protein can be considered to be divided into the following domains (starting at the amino terminal and ending at the carboxy terminal of the polypeptide):

- signal peptide (amino acids −21 to −1)—this is cleaved off in human cells during the transport of the receptor to the cell surface and thus does not constitute part of the mature, active receptor;
- immunoglobulin (Ig)-like domain (approximately amino acids 1-115)—this domain assumes a structure, referred to as the immunoglobulin fold, which is similar to those of many other molecules involved in regulating the immune system, the immunoglobulin family of proteins. The crystal structure of the CD8αα receptor in complex with the human MHC molecule HLA-A2 has demonstrated how the Ig domain of CD8αα receptor binds the ligand;
- membrane proximal stalk region (amino acids 116-160)—this domain is thought to be an extended linker region allowing the CD8αα receptor to "reach" from the surface of the T-cell over the top of the MHC to the a3 domain of the MHC where it binds. The stalk region is glycosylated and thought to be inflexible;
- transmembrane domain (amino acids 161-188)—this anchors the CD8αα receptor in the cell membrane and is therefore not part of the soluble recombinant protein;
- cytoplasmic domain (amino acids 189-214)—this mediates a signalling function in T-cells through its association with $p56^{lck}$ which is involved in the T cell activation cascade of phosphorylation events.

In the present invention, the CD8 molecule generally has a sufficient portion of the immunoglobulin domain to be able to bind to MHC. Generally, the molecule will comprise all or a substantial part of the native CD8α immunoglobulin domain, but may comprise at least 10, 15, 20, 25, 30, 35, 40, 45, 50, 55, 60, 65, 70, 75, 80, 85, 90, 95, 100, 105, 110 or 115 amino acids of the immunoglobulin domain. The molecules of the present invention are preferably dimers (i.e. αα or αβ), although CD8α monomer are included within the scope of the present invention. In αα dimer molecules of the present invention it is preferred if both α chains carry the $Ser_{53}$ mutation.

The CD8 molecule may be a soluble form of the native CD8 molecule. The term "soluble form" is used herein in relation to the CD8 molecule in the manner in which it is conventionally used in the art in relation to cell surface receptors. A soluble form of a cell surface receptor is usually derived from the native form by deletion of the transmembrane domain. The protein may be truncated by removing both the cytoplasmic and the transmembrane domains, or there may be deletion of just the transmembrane domain with part or all of the cytoplasmic domain being retained. The protein may be modified to achieve the desired soluble form by proteolytic cleavage, or by expressing a genetically engineered truncated or partially deleted form. In one embodiment, the CD8 molecule of the present invention is a monomer or a homodimer of a polypeptide which comprises residues 1-120, except of course that $Ser_{53}$ is mutated as described above. Alternatively, it may be a heterodimer of such a polypeptide and a soluble form of the CD8β chain, for example as shown in FIG. 1d. In a further embodiment, $Cys_{33}$ of at least one α chain thereof is mutated to Ser or Ala. This mutation prevents the formation of inappropriate inter- or intra-chain disulphide bonds between $Cys_{33}$ and the other Cys residues ($Cys_{22}$ and $Cys_{94}$). As a result, this mutant has increased yield on expression and/or refolding. One CD8 molecule of the present invention is a monomer or a homodimer of a polypeptide which has the amino acid sequence as shown in FIG. 1b. Another is a heterodimer of such a polypeptide and a polypeptide having the amino acid sequence of FIG. 1d.

It is however not essential that the CD8 molecule of the present invention is soluble, especially when the molecule is intended to be administered using gene therapy. Such molecules may comprise all or part of the signal peptide and/or cytoplasmic and/or transmembrane domains. In one embodiment, the CD8 molecule of the present invention comprises residues 1-214 as shown in FIG. 1c. In another embodiment, the CD8 molecule lacks the transmembrane domain (residues 161-188) and/or includes the signal peptide. Homodimers of such molecules and heterodimers with corresponding β chains are also included within the scope of the invention.

Also included within the scope of the invention are the CD8 molecules described above with one or more of the following variations.

Variations of the C-terminal truncation point. Longer or shorter versions of the receptor may be stable and functional. For soluble forms, there is no general rule to predict where the optimal truncation point for a soluble version of a transmembrane protein is. In the case of CD8, the polypeptide could be between 1 and 15 amino acids longer or shorter. However, when shortened at the C-terminus, the molecule still retains a short fragment of the membrane-proximal stalk region. The soluble CD8 could even comprise the cytoplasmic domain, having just the transmembrane domain deleted. It is also envisaged that the C-terminus could be fused to peptides or protein domains, such as glutathione-S-transferase, for purification purposes, or to a label for detection, as is well known in the art. In the case of the protein of FIG. 1b, 1-15 amino acid residues may be absent from the C-terminus, but with at least a part of the membrane-proximal stalk region, i.e. the region defined by amino acids 116-120, retained; all or part of the sequence "ala-pro-arg-pro-pro-thr-pro-ala" (SEQ ID NO:10) may be added at the C-terminus; and/or all or part of the CD8 cytoplasmic membrane peptide sequence may be added at the C-terminus.

Variations in the N-terminal truncation point. The N-terminal truncation point could be varied, just like the C-terminal truncation point, without any influence on the functional effect of the protein. It is also envisaged that the N-terminus could be fused to peptides or protein domains, such as glutathione-S-transferase, for purification purposes, or to a label for detection, as is well known in the art. In the case of the protein of FIG. 1b, methionine may be present at the N-terminus; 1-15 amino acid residues may be absent from the N-terminus; and/or all or part of the sequence "leu-leu-leu-his-ala-ala-arg-pro" (SEQ ID NO:11) may be added to the N-terminus.

Conservative amino acid substitutions. A large number of conservative amino acid substitutions can be introduced in the protein without causing any significant changes. Thus, it may be possible to replace one amino acid with another of similar "type", for instance, replacing one hydrophobic amino acid with another. In the case of such homologues and derivatives, the degree of identity with a modified CD8 as described above is less important than that the homologue or derivative should retain a mutation of $Ser_{53}$ and an enhanced binding to MHC is enhanced compared to wild type CD8. However, suitably, homologues or derivatives having at least 60% identity are provided. Preferably, homologues or derivatives having at least 70% identity, more preferably at least 80% identity are provided. Most preferably, homologues or derivatives having at least 90% or even 95% identity are provided.

The percent identity of two amino acid sequences or of two nucleic acid sequences is determined by aligning the sequences for optimal comparison purposes (e.g. gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. The NBLAST and XBLAST programs of Altschul, et al. (1990) *J. Mol. Biol.* 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) *Nucleic Acids Res.* 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) *Comput. Appl. Biosci.*, 10:3-5; and FASTA described in Pearson and Lipman (1988) *Proc. Natl. Acad. Sci.* 85:2444-8. Within FASTA, ktup is a control option that sets the sensitivity and speed of the search.

More particularly, the invention provides a soluble CD8αα or ββ molecule containing a substantial part of the extracellular region of CD8, including the immunoglobulin domain and a fragment of the membrane proximal stalk region, which CD8 molecule is not disulphide-linked between the two chains of the molecule, wherein $Ser_{53}$ of at least one α chain thereof is mutated as described above.

The CD8 molecules described herein may be in the form of a multimer, that is two or more CD8 monomer or dimer (αα or αβ) molecules linked (covalently or otherwise) together. The CD8 molecules may be associated with one another via a linker molecule. Alternatively or additionally, the CD8 molecules may be attached to larger entities such as membrane structures or particles.

Suitable linker molecules include multivalent attachment molecules such as avidin, streptavidin and extravidin, each of which has four binding sites for biotin. Thus, biotinylated CD8 molecules can be formed into multimer complexes of CD8 having a plurality of CD8 binding sites. The number of CD8 molecules in the resulting complex will depend upon the quantity of CD8 in relation to the quantity of linker molecule used to make the complexes, and also on the presence or absence of any other biotinylated molecules. Preferred complexes are trimeric or tetrameric CD8 complexes. One or both chains of the CD8 molecule are preferably biotinylated, conveniently by means of a biotinylation sequence expressed as a tag on the α or β chain. A preferred multimer is a tetramer with three mutant CD8 molecules and a fourth molecule, which may be a co-stimulatory agent, such as CD28 or CTLA-4.

Suitable structures for attachment of soluble CD8, optionally already in multimeric form, include membrane structures such as liposomes and solid structures which are preferably particles such as beads. Other structures known to those skilled in the art which may be externally coated with CD8 molecules are also suitable.

A modified CD8 molecule of the present invention may be provided in substantially pure form. For example, it may be provided in a form which is substantially free of other proteins. The modified CD8 molecules of the present invention can be provided alone, as a purified or isolated preparation. They may be provided as part of a mixture with one or more other molecules of the invention.

The following tests for enhanced MHC binding for modified CD8 molecules of the present invention compared to the wild-type molecule can be performed. The binding of soluble modified CD8 molecules to MHC can be determined by following the method detailed in Example 14 herein. The binding of full length modified CD8 molecules to MHC can conveniently be determined using the cell adhesion method detailed in Salter et al., Nature 338 (6213) 345-347. Briefly, this method involves expression of the modified CD8 molecule in a monolayer of CHO cells and monitoring the binding of APCs to the CD8 expressing CHO cells. For both of these tests the MHC binding affinity determination should by the average of three experiments.

Gene cloning techniques maybe used to provide a modified CD8 molecule of the invention. These techniques are disclosed, for example, in J. Sambrook et al, *Molecular Cloning* 2nd Edition, Cold Spring Harbor Laboratory Press (1989). Thus, the present invention provides a nucleic acid, particularly a DNA, comprising a sequence which:
  (i) encodes a modified CD8 molecule as defined herein;
  (ii) is an RNA equivalent of the DNA of (i);
  (iii) is complementary to the sequences of (i) or (ii); or
  (iv) has substantial identity with the sequences of (i), (ii) or (iii).

In one embodiment of this aspect of the invention, the nucleic acid has the DNA sequence set out in FIG. 1*b* or 1*c* with or without the signal sequence herein. The term "RNA equivalent" when used above indicates that a given RNA molecule has a sequence which is complementary to that of a given DNA molecule (allowing for the fact that in RNA "U" replaces "T" in the genetic code).

The nucleic acid molecules of the invention may include a plurality of such sequences. The skilled person will appreciate that the present invention can include novel variants of those particular novel nucleic acid molecules which are exemplified herein. Such variants are encompassed by the present invention. For example, additions, substitutions and/or deletions are included. In addition, and particularly when utilising microbial expression systems, one may wish to engineer the nucleic acid sequence by making use of known preferred codon usage in the particular organism being used for expression. Thus, synthetic or non-naturally occurring variants are also included within the scope of the invention.

Preferably, sequences which have substantial identity have at least 50% sequence identity, desirably at least 75% sequence identity and more desirably at least 90 or at least 95% sequence identity with said sequences. In some cases, the sequence identity may be 99% or above. Desirably, the term "substantial identity" indicates that said sequence has a greater degree of identity with any of the sequences described herein than with prior art nucleic acid sequences. Substantially identical sequences may hybridise with the sequences described above under moderate or highly stringent hybridising conditions. For a high degree of selectivity, relatively stringent conditions are used to form the duplexes, such as low salt or high temperature conditions. As used herein, "highly stringent conditions" means hybridisation to filter-bound DNA in 0.5 M $NaHPO_4$, 7% sodium dodecyl sulphate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3) For some applications, less stringent conditions for duplex formation are required. As used herein "moderately stringent conditions" means washing in 0.2×SSC/0.1% SDS at 42° C. (Ausubel et al., 1989, supra). Hybridisation conditions can also be rendered more stringent by the addition of increasing amounts of formamide, to destabilise the hybrid duplex. Thus, particular hybridisation conditions can be readily manipulated, and will generally be chosen depending on the desired results.

The nucleic acid molecules of the invention may be in isolated or recombinant form. They may be incorporated into a vector and the vector may be incorporated into a host cell. Such vectors and suitable hosts form yet further aspects of the present invention.

The invention provides, in a still further aspect, a method of producing a modified CD8 molecule of the invention, which method comprises the steps of: i) effecting expression of a nucleic acid molecule of the present invention in a bacterium or eukaryotic cell and recovering the expressed protein from a cell culture; and ii) treating the expressed protein to facilitate its purification and carrying out said purification. Preferably, the nucleic acid is modified via silent mutations designed to increase expression via the prevention of the formation of a 5' hairpin secondary structure in the expressed mRNA. Preferably at step iii), the treatment of the expressed protein involves solubilising the protein and treating the protein so as to cause it to fold into a form resembling its native state, which is then purified. Where the CD8 molecule is an αβ heterodimer, the nucleic acid sequence of FIG. 1d may be expressed in addition to the mutant α chain.

A means of producing soluble CD8αα and CD8αβ in CHO cells for use in ligand binding studies is known (Pellicci et al., 2000 J. Immunol. Methods 246 (1-2) p149-163). Briefly, co-expression of CDα with CD8β led to CD8αβ expression, which was secreted as a non-covalent heterodimer at 3 mg/l in the presence of CD8αα. In order to separate the CD8α homodimer from the CD8αβ heterodimer, affinity chromatographic techniques specific for the CD8β subunit were employed. The inclusion of a hexahistidine tag at the C-terminus of CD8β enabled affinity purification of soluble CD8αβ (and sCD8αα) under neutral conditions, yielding recombinant protein with the correct stoichiometry and full antigenic activity. This production method is expected to be suitable for the production of CD8αβ heterodimers of the present invention.

Modified CD8 molecules of the present invention can be expressed as soluble recombinant protein for extracellular addition, or expressed intracellularly by transfection of a DNA construct encoding the modified CD8 molecule. Transfection of DNA can be achieved both in vitro as well as in vivo, for example by using various type of recombinant viruses as vehicles for DNA transformation or by transfection techniques that use "naked" DNA. For example, an organ to be transplanted may be incubated in a modified CD8 molecule of the present invention to make it more difficult for the immune system of host to recognise and reject it.

The ability of soluble CD8, delivered in addition to chloramphenical acetyl transferase (CAT) via transfection of mice with an adenovirus vector, to inhibit CD8+ T cell proliferation and responses in vivo has been demonstrated. (Peng et al, (2000) *Journal of Immunology* 165:1470-1478). The results of this study demonstrate that transgenic soluble CD8 continues to be present in the blood of the mice at least 28 after injection. The ability of intrahepatic CTLs, target cells taken from mice 10 days after injection, to lyse CAT-infected C57SV was also assessed. The cells from mice transfected with soluble CD8 resulted in specific lysis of the target cells a factor of 4 times lower than T cells from control mice at an E:T ratio of 10:1.

Preferably in gene therapy, the modified CD8 molecules of the present invention are administered such that they are expressed in the subject to be treated, for example in the form of a recombinant DNA molecule comprising a polynucleotide encoding the modified CD8 molecule of the present invention operatively linked to a nucleic acid sequence which controls expression, such as in an expression vector. Such a vector will thus include appropriate transcriptional control signals including a promoter region capable of expressing the coding sequence, said promoter being operable in the subject to be treated. Thus for human gene therapy, the promoter, which term includes not only the sequence necessary to direct RNA polymerase to the transcriptional start site, but also, if appropriate, other operating or controlling sequences including enhancers, is preferably a human promoter sequence from a human gene, or from a gene which is typically expressed in humans, such as the promoter from human cytomegalovirus (CMV). Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

A polynucleotide sequence and transcriptional control sequence may be provided cloned into a replicable plasmid vector, based on commercially available plasmids, such as pBR322, or may be constructed from available plasmids by routine application of well known, published procedures.

The vector may also include transcriptional control signals, situated 3' to the modified CD8 molecule encoding sequence, and also polyadenylation signals, recognisable in the subject to be treated, such as, for example, the corresponding sequences from viruses such as, for human treatment, the SV40 virus. Other transcriptional controlling sequences are well known in the art and may be used.

The expression vectors may also include selectable markers, such as for antibiotic resistance, which enable the vectors to be propagated.

Expression vectors capable in situ of synthesising modified CD8 molecules of the present invention may be introduced directly by physical methods. Examples of these include topical application of the "naked" nucleic acid vector in an appropriate vehicle for example in solution in a pharmaceutically acceptable excipient, such as phosphate buffered saline (PBS). Other physical methods of administering the DNA directly to the recipient include ultrasound, electrical stimulation, electroporation and microseeding.

Nucleic acid sequence encoding modified CD8 molecules of the present invention for use in the therapy of the invention may also be administered by means of delivery vectors. These include viral delivery vectors, such as adenovirus or retrovirus delivery vectors known in the art. Other non-viral delivery vectors include lipid delivery vectors, including liposome delivery vehicles, known in the art.

Such a nucleic acid sequence may also be administered by means of transformed host cells. Such cells include cells harvested from the subject, into which the nucleic acid sequence is introduced by gene transfer methods known in the art, followed by growth of the transformed cells in culture and administration to the subject.

Expression constructs such as those described above may be used in a variety of ways in the therapy of the present invention. Thus, they may be directly administered to the subject, or they may be used to prepare modified CD8 molecules of the present invention, which can then be administered as is discussed in more detail below. The invention also relates to host cells which are genetically engineered with constructs which comprise polynucleotide encoding modified CD8 molecules of the present invention, and to the uses of these vectors and cells in the therapeutic methods of the invention. These constructs may be used per se in the therapeutic methods of the invention or they may be used to prepare a modified CD8 molecule of the present invention for use in the therapeutic methods of the invention described in greater detail below.

The vector may be, for example, a plasmid vector, a single or double-stranded phage vector, a single or double-stranded RNA or DNA viral vector, depending upon whether the vector is to be administered directly (i.e. for in situ synthesis), or is to be used for synthesis of a modified CD8 molecule. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Generally, vectors for expressing a modified CD8 molecule of the present invention for use in the invention comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain embodiments in this regard, the vectors provide for specific expression. For production of modified CD8 molecules of the present invention, such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express modified CD8 molecules for use in the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, adeno-associated viruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

The nucleic acid sequence in the expression vector may be operatively linked to appropriate expression control sequence(s), including, for instance, a promoter to direct mRNA transcription. Representatives of such promoters include, but are not limited to, the phage lambda PL promoter, the *E. coli* lac, trp and tac promoters, for recombinant expression, and the SV40 early and late promoters and promoters of retroviral LTRs for in situ expression.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly-practised procedures, such regions will operate by controlling transcription, such as transcription factors, repressor binding and termination sites, among others.

Vectors for propagation and expression generally will include selectable markers and amplification regions, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

Representative examples of appropriate hosts for recombinant expression of CD8 molecules of the present invention include bacterial cells, such as *streptococci, staphylococci, E. coli, streptomyces* and *Bacillus subtilis* cells; fungal cells, such as yeast cells and *Aspergillus* cells; insect cells such as *Drosophila* S2 and *Spodoptera* Sf9 cells; animal or human cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and pSVL available from Pharmacia. These vectors which can be used both for recombinant expression and for in situ expression are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide for use in the therapy of the invention in a host may be used in this aspect of the invention.

Examples of vectors for use in this aspect of the invention include expression vectors in which cDNA sequence encoding a modified CD8 molecule of the present invention is inserted in a plasmid whereby gene expression is driven from the human immediate early cytomegalovirus enhancer-promoter (Foecking and Hofstetter, *Cell,* 45, 101-105, 1986). Such expression plasmids may contain SV40 RNA processing signals such as polyadenylation and termination signals. Expression constructs which use the CMV promoter and that are commercially available are pCDM8, pcDNA1 and derivatives, pcDNA3 and derivatives (Invitrogen). Other expression vectors available which may be used are pSVK3 and pSVL which contain the SV40 promoter and mRNA splice site and polyadenylation signals from SV40 (pSVK3) and SV40 VP1 processing signals (pSVL; vectors from Pharmacia).

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides for use in the therapy of the present invention include not only well known and readily available promoters, but also promoters that readily may be obtained by the foregoing technique, using a reporter gene; for in situ expression, such a promoter should be recognised in the subject to be treated.

Among known prokaryotic promoters suitable for expression of polynucleotides and polypeptides in accordance with the therapy of the present invention are the *E. coli* lacI and lacZ and promoters, the T3 and T7 promoters, the gpt promoter, the lambda PR, PL promoters and the trp promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides for use in the therapy of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide when recombinantly synthesised. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, a region may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunoglobulin that is useful to solubilise or purify polypeptides. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Mammalian expression vectors may comprise an origin of replication, a suitable promoter and enhancer, and also any necessary ribosome binding sites, polyadenylation regions, splice donor and acceptor sites, transcriptional termination sequences, and 5' flanking non-transcribed sequences that are necessary for expression.

For preparing a modified CD8 molecule of the present invention, genetically engineered host cells may be used. Introduction of a polynucleotide into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989).

Mature proteins can be expressed in host cells including mammalian cells such as CHO cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Binding of CD8 to MHC/peptide complexes can be conveniently detected by surface plasmon resonance studies, for instance on the Biacore2000 or Biacore3000 systems (Garcia, et al. *Nature* 384:577-81 Issn: 0028-0836 (1996); Wyer, et al. *Immunity* 10: 219-225 (1999)). The production of soluble MHC-peptide complexes is well known. Soluble MHC-peptide complexes were first obtained by cleaving the molecules of the surface of antigen presenting cells with papain (Bjorkman, et al. *J Mol Biol* 186: 205-10 (1985)). Although this approach provided material for crystallisation, it has, for class I molecules, in recent years been replaced by individual expression of heavy and light chain in *E. coli* followed by refolding in the presence of synthetic peptide (Gao, et al. *Prot. Sci.* 7: 1245-49 (1998); Gao, et al. *Nature* 387: 630-4 (1997); Garboczi, et al. *Proc Natl Acad Sci USA* 89: 3429-33 Issn: 0027-8424 (1992); Garboczi, et al. *J Mol Biol* 239: 581-7 Issn: 0022-2836 (1994); Madden, et al. [published erratum appears in Cell 1994 Jan. 28;76(2): following 410]. *Cell* 75: 693-708 Issn: 0092-8674 (1993); Reid, et al. *J Exp Med* 184: 2279-86 (1996); Reid, et al. *FEBS Lett* 383: 119-23 (1996); Smith, et al. *Immunity* 4: 215-28 Issn: 1074-7613 (1996); Smith, et al. *Immunity* 4: 203-13 Issn: 1074-7613 (1996)). This approach has several advantages over previous methods in that a better yield is obtained at a lower cost, peptide identity can be controlled very accurately, and the final product is more homogenous. Furthermore, expression of modified heavy or light chain, for instance fused to a protein tag, can be easily performed.

The inhibitory effects of modified CD8 molecules of the present invention can also be tested in in vitro CTL assays in order to assess their inhibitory effect on T cell activation. These studies can be extended to in vivo analysis of the effects of the modified CD8 molecules by testing these in relevant animal disease models.

The modified CD8 molecules of the invention, and the nucleic acids encoding them, find particular use in the treatment of patients requiring immunosuppressive therapy. Such patients include transplant patients, either awaiting transplant, undergoing transplantation or after transplantation has taken place. Autoimmune diseases (such as those described herein) and allergies may also usefully be treated by immunosuppressive therapy. One specific example is exacerbated asthma in which T cells come into play as a result of viral infection. Severe damage to the lungs follows and the result is chronic asthma which can lead to death. The current treatment is with corticosteroids which strongly suppress the immune system. A preferable treatment is one which suppresses the immune system more selectively, such as specific blocking of CTL function by modified CD8 as described herein.

The modified CD8 will be administered in a manner appropriate for the condition to be treated or prevented. For example, for prevention of graft rejection one or more injections into the local area concerned may be most suitable. On the other hand, for an autoimmune disease where the effects are throughout the body, it may be more appropriate to inject the modified CD8 directly into the bloodstream.

Suitable compositions and dosage of modified CD8 as an immunosuppressive agent can be devised by one of ordinary skill in the art. Two or more doses of a smaller amount of modified CD8 may be preferable to a single high level dose. Formulations may be for example liquid formulations, or powder formulations such as those designed for delivery by a high velocity needle-less delivery device.

The compositions according to the invention may further comprise, or be administered in a treatment regime with, other agents, in particular, other immunosuppressive agents. Thus, the invention provides a product containing a modified CD8 molecule as described herein or a nucleic acid encoding such a modified CD8 molecule and an immunosuppressive agent as a combined preparation for simultaneous, sequential or separate use in inhibiting $CD8^+$ T cell response.

The most commonly-used immunosuppressive drugs currently include corticosteroids and more potent inhibitors like, for instance, methotrexate, sulphasalazine, hydroxychloroquine, 6-MP/azathioprine and cyclosporine (Baert & Rutgeerts, 1997, *Acta Clin. Belg.* 52: 251-7; Singer & McCune, 1998, *Curr Opin Rheumatol,* 10: 169-73). All of these treatments have severe side-effects related to toxicity, however, and the need for drugs that would allow their elimination from, or reduction in, use is urgent (McKendry, 1997, *Rheum Dis ClinNorth Am,* 23: 939-54; Ortiz et al., 1998, *J. Rheumatol,* 25: 36-43; Sibilia et al., 1998, *Rev Rhum Engl Ed* 65: 267-73; Singer & McCune, 1998, *Curr Opin Rheumatol,* 10: 169-73). Many immunosuppressive drugs have been found to have greater efficacy when used in combination, even when the total dose is lowered (Verhoeven et al., 1998, *Br J Rheumatol,* 37: 612-9).

Other immunosuppressive drugs include the gentler, but less powerful non-steroid treatments such as Aspirin and Ibuprofen, and a new class of reagents which are based on more specific immune modulator functions. This latter class includes interleukins, cytokines, recombinant adhesion molecules and monoclonal antibodies (for reviews see Baert & Rutgeerts, 1997, *Acta Clin. Belg.* 52: 251-7; Chatenoud, 1998, *Mol Med Today,* 4: 25-30).

CD8αα is specific for class I MHC molecules and is therefore expected to inhibit only the response of cytotoxic or memory T cells to target cells presenting class I complexes. Many cellular immune responses are of a composite nature, involving class I and class II-restricted T cells. In some situations, it may be desirable to use modified CD8αα on its own to suppress unwanted CTL responses. In many situations, modified CD8αα may be useful in combination with other immunosuppressive drugs or reagents which suppress other elements of the immune response.

It is envisaged that including modified CD8 in an immunosuppressive treatment protocol will increase the efficiency of immunosuppression, and particularly, may enable the administered amounts of other drugs, which have toxic or other adverse effects to be decreased.

Medicaments in accordance with the invention will usually be supplied as part of a sterile, pharmaceutical composition which will normally include a pharmaceutically acceptable carrier. This pharmaceutical composition may be in any suitable form, (depending upon the desired method of administering it to a patient).

It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions)

Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6): 318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substances of the present invention can vary between wide limits, depending upon the disease or disorder to be treated, the age and condition of the individual to be treated, etc. and a physician will ultimately determine appropriate dosages to be used. The dosage may be repeated as often as appropriate. If side effects develop the amount and/or frequency of the dosage can be reduced, in accordance with normal clinical practice.

In a further aspect, the soluble CD8 mutants described herein find application as a screening reagent. The relatively weak affinity of native soluble CD8 for HLA molecules places stringent requirements on the technology required to screen for inhibition of the CD8-HLA interaction. Many high throughput screen (HTS) assays involve homogenous methodologies, such as homogeneous time resolved fluorescence (HTRF). Such techniques have drawbacks when approaching low affinity interactions, as they require relatively high concentrations of the radioactive or fluorescent tracer molecules, typically resulting in low signal to background ratios. The relatively high affinity of the CD8 mutants described herein for HLA can result in a higher responses and improved signal to noise ratios. The AlphaScreen™ (Amplified Luminescent Proximity Homogenous Assay), recently developed by Packard, is a non-radioactive homogeneous assay technology specifically applicable to low affinity interactions. This technique provides an attractive option on which to base HTS assays for the identification of inhibitors of interactions between TCR/CD8 and CD8/HLA.

Preferred features of each aspect of the invention are as for each of the other aspects mutatis mutandis. The prior art documents mentioned herein are incorporated to the fullest extent permitted by law.

EXAMPLES

Example 1

$Ser_{53} \rightarrow Asn$ Mutation of Human $sCD8\alpha\alpha$

This example describes the construction of a DNA expression plasmid, pEX103, that codes for a CD8α recombinant protein in which $Serine_{53}$ is substituted for Asparagine.

A DNA plasmid, pBJ112 (described in WO 99/21576) encodes amino acids 1-120 of human CD8α in which the signal peptide is substituted for a single Methionine residue in order to allow initiation of translation when expressed in bacteria.

pEX103 was generated as follows. PCR mutagenesis was performed with pBJ112 as a template with the following primers in order to produce the $Ser_{53} \rightarrow Asn$ mutant of soluble CD8α:

```
                                        (SEQ ID NO:12)
Amino Acid      Leu Leu Tyr Leu Asn Gln Asn Lys (SEQ ID NO:13)
Forward:    5'  CTC CTA TAC CTC AAC CAA AAC AAG CC (SEQ ID NO:14)
Reverse:    5'  GG CTT GTT TTG GTT GAG GTA TAG GAG
```

Bases shown in bold indicate the codons that were changed to produce the $Ser_{53} \rightarrow Asn$ substitution. The bases which were changed in these codons are underlined.

25 ng of plasmid pBJ112 was mixed with 5 µl 10 mM dNTP, 25 µl 10×Pfu-buffer (Stratagene), 10 units Pfu polymerase (Stratagene) and the final volume was adjusted to 240 µl with $H_2O$. 48 µl of this mix was supplemented with 125 ng of each primer diluted to give a final concentration of 0.2 µM in 50 µl final reaction volume. After an initial denaturation step of 2 minutes at 95° C. the reaction mixture was subjected to 18 rounds of denaturation (95° C., 30 sec.), annealing (55° C., 60 sec.), and elongation (68° C., 10 min.) in a Hybaid PCR express PCR machine. The product was then digested for 90 minutes at 37° C. with 10 units of DpnI restriction enzyme (New England Biolabs) in order to remove the methylated pBJ112 template plasmid. 10 µl of the digested reaction was transformed into XL1-Blue bacteria and grown for 18 hours at 37° C. on a plate. A single colony was picked and grown over night in 5 ml TYP+Ampicillin (16 g/l Bacto-Tryptone, 16 g/l Yeast Extract, 5 g/l NaCl, 2.5 g/l $K_2HPO_4$, 100 mg/l Ampicillin). Plasmid DNA was purified on a Qiagen miniprep column according to the manufacturer's instructions and the sequence was verified by automated sequencing at the sequencing facility of Department of Biochemistry, Oxford University.

Example 2

$Gln_2 \rightarrow Lys$ Mutation of Human $sCD8\alpha\alpha$

This example describes the construction of a DNA expression plasmid, pLX106, that codes for $sCD8\alpha\alpha$ in which $Glutamine_2$ is substituted for Lysine. The DNA sequences of the primers used are shown below:

```
Amino Acid:                         (SEQ ID NO:15)
    Asp Ile His Met Ser Lys Phe Arg Val Forward:                            (SEQ ID NO:16)
5' GAT ATA CAT ATG AGT AAA TTT CGT GTA TC
```

```
Reverse:                                      (SEQ ID NO:17)
     5' GA TAC ACG AAA TTT ACT CAT ATG TAT ATC
```

Mutation of DNA plasmid pBJ112 was carried out according to the same protocol as described in Example 1, and the sequence was verified by automated sequencing at the sequencing facility of Department of Biochemistry, Oxford University.

Example 3

Asn$_{28}$→Gln Mutation of Human sCD8αα

This example describes the construction of the DNA expression plasmid, pEX107, that codes for sCD8αα in which Asparagine$_{28}$ is substituted for Glutamine. The DNA sequences of the primers used are shown below:

```
                                              (SEQ ID NO:18)
Amino Acid:         Leu Leu Ser Gln Pro Thr Ser (SEQ ID NO:19)
Forward:       5' G CTG CTG TCC CAG CCG ACG TCG G (SEQ ID NO:20)
Reverse:       5' C CGA CGT CGG CTG GGA CAG CAG C
```

Mutation of DNA plasmid pBJ112 was carried out according to the same protocol as described in Example 1, and the sequence was verified by automated sequencing at the sequencing facility of Department of Biochemistry, Oxford University.

Example 4

Phe$_{48}$→Glu Mutation of Human sCD8αα

This example describes the construction of a DNA expression plasmid, pEX108, that codes for sCD8αα in which Phenylalanine$_{48}$ is substituted for Glutamic acid. The DNA sequences of the primers used are shown below:

```
                                              (SEQ ID NO:21)
Amino Acid:         Ser Pro Thr Glu Leu Leu Tyr (SEQ ID NO:22)
Forward:       5' CC AGT CCC ACC GAA CTC CTA TAC C (SEQ ID NO:23)
Reverse:       5' G GTA TAG GAG TTC GGT GGG ACT GG
```

Mutation of DNA plasmid pBJ112 was carried out according to the same protocol as described in Example 1, and the sequence was verified by automated sequencing at the sequencing facility of Department of Biochemistry, Oxford University.

Example 5

Leu$_{97}$→Tyr Mutation of Human sCD8αα

This example describes the construction of a DNA expression plasmid, pEX109, that codes for sCD8αα in which Leucine$_{97}$ is substituted for Tyrosine. The DNA sequences of the primers used are shown below:

```
                                              (SEQ ID NO:24)
Amino Acid:         Cys Ser Ala Tyr Ser Asn Ser (SEQ ID NO:25)
Forward:       5' TC TGC TCG GCC TAT AGC AAC TCC A (SEQ ID NO:26)
Reverse:       5' T GGA GTT GCT ATA GGC CGA GCA GA
```

Mutation of DNA plasmid pBJ112 was carried out according to the same protocol as described in Example 1, and the sequence was verified by automated sequencing at the sequencing facility of Department of Biochemistry, Oxford University.

Example 6

Leu$_{97}$→Gln Mutation of Human sCD8αα

This example describes the construction of a DNA expression plasmid, pEX110, that codes for sCD8αα in which Leucine$_{97}$ is substituted for Glutamine. The DNA sequences of the primers used are shown below:

```
                                              (SEQ ID NO:27)
Amino Acid:         Cys Ser Ala Gln Ser Asn Ser (SEQ ID NO:28)
Forward:       5' C TGC TCG GCC CAG AGC AAC TCC (SEQ ID NO:29)
Reverse:       5'   GGA GTT GCT CTG GGC CGA GCA G
```

Mutation of DNA plasmid pBJ112 was carried out according to the same protocol as described in Example 1, and the sequence was verified by automated sequencing at the sequencing facility of Department of Biochemistry, Oxford University.

Example 7

Leu$_{97}$→Ser Mutation of Human sCD8αα

This example describes the construction of a DNA expression plasmid, pEX111, that codes for sCD8αα in which Leucine$_{97}$ is substituted for Serine. The DNA sequences of the primers used are shown below:

```
                                              (SEQ ID NO:30)
Amino Acid:         Cys Ser Ala Ser Ser Asn Ser (SEQ ID NO:31)
Forward:       5' C TGC TCG GCC TCG AGC AAC TCC A (SEQ ID NO:32)
Reverse:       5' T GGA GTT GCT CGA GGC CGA GCA G
```

Mutation of DNA plasmid pBJ112 was carried out according to the same protocol as described in Example 1, and the sequence was verified by automated sequencing at the sequencing facility of Department of Biochemistry, Oxford University.

Example 8

Asn$_{99}$→Ile Mutation of Human sCD8αα

This example describes the construction of a DNA expression plasmid pEX112 that codes for sCD8αα in which Asparagine₉₉ is substituted for Isoleucine. The DNA sequences of the primers used are shown below:

```
                                        (SEQ ID NO:33)
Amino Acid:        Ala Leu Ser Ile Ser Ile Met (SEQ ID NO:34)
Forward:       5' CG GCC CTG AGC ATC TCC ATC ATG T (SEQ ID NO:35)
Reverse:       5' A CAT GAT GGA GAT GCT CAG GGC CG
```

Mutation of DNA plasmid pBJ112 was carried out according to the same protocol as described in Example 1, and the sequence was verified by automated sequencing at the sequencing facility of Department of Biochemistry, Oxford University.

Example 9

Asn₉₉→Met Mutation of Human sCD8αα

This example describes the construction of a DNA expression plasmid, pEX113, that codes for sCD8αα in which Asparagine₉₉ is substituted for Methionine. The DNA sequences of the primers used are shown below:

```
                                        (SEQ ID NO:36)
Amino Acid:        Ala Leu Ser Met Ser Ile Met (SEQ ID NO:37)
Forward:       5'  G GCC CTG AGC ATG TCC ATC ATG TA (SEQ ID NO:38)
Reverse:       5' TA CAT GAT GGA CAT GCT CAG GGC C
```

Mutation of DNA plasmid pBJ112 was carried out according to the same protocol as described in Example 1, and the sequence was verified by automated sequencing at the sequencing facility of Department of Biochemistry, Oxford University.

Example 10

Cys₃₃→Ala Mutation of Human sCD8αα

This example describes the construction of the DNA expression plasmid pEX115 that codes for the sCD8αα in which Cysteine₃₃ is substituted for Alanine. The DNA sequences of the primers used are shown below (nucleotide substitutions are indicated in bold):

```
                                        (SEQ ID NO:39)
Amino Acid:        Thr Ser Gly Ala Ser Trp Leu (SEQ ID NO:40)
Forward:       5'-G ACG TCG GGC GCC TCG TGG CTC-3'

(SEQ ID NO:41)
Reverse:       5'-GAG CCA CGA GGC GCC CGA CGT C-3'
```

Mutation of DNA plasmid pBJ112 was carried out according to the same protocol as described in Example 1 and the sequence was verified by automated sequencing at the sequencing facility of Department of Biochemistry, Oxford University.

Example 11

Cys₃₃→Ser Mutation of Human sCD8αα

This example describes the construction of the DNA expression plasmid pJMB017 that codes for the sCD8αα in which Cysteine₃₃ is substituted for Serine. The DNA sequences of the primers used are shown below (nucleotide substitutions are indicated in bold):

```
                                        (SEQ ID NO:42)
Amino Acid:        Thr Ser Gly Ser Ser Trp Leu (SEQ ID NO:43)
Forward:       5'-G ACG TCG GGC AGC TCG TGG CTC-3'

(SEQ ID NO:44)
Reverse:       5'-GAG CCA CGA GCT GCC CGA CGT C-3'
```

Mutation of DNA plasmid pBJ112 was carried out according to the same protocol as described in Example 1 and the sequence was verified by automated sequencing at the sequencing facility of Department of Biochemistry, Oxford University.

Example 12

Expression, Refolding and Purification of Human sCD8αα Mutants sCD8α protein was expressed from the DNA vector pBJ112 and from mutated derivatives of pBJ112, i.e. pEX013, pEX106-113, PEX115 and pJMB107, in the *E. coli* strain BL21-DE3 pLysS (Novagen). pBJ112 contains the sCD8α gene under the control of the strongly inducible T7 promoter in the vector pGMT7 (Studier, et al. *Methods in Enzymology* 185: 60-89 ISSN: 0076-6879 (1990)). BL21 cells transformed with the sCDα expressing vectors were plated on LB/agar/100 mg/l Ampicillin plates made according to a standard recipe. Transformants were then grown in TYP medium with Ampicillin (16 g/l Bacto-Tryptone, 16 µl Yeast Extract, 5 g/l NaCl, 2.5 g/l K₂HPO₄, 100 mg/l Ampicillin) to an OD₆₀₀~0.5 (RANGE 0.4-0.6). For large-scale expression, 1 l volumes of TYP media were prepared in 2 l conical flasks and were covered with four layers of aluminium foil and were autoclaved. Cell densities were measured using optical density at 600 nm wavelength (OD600) on a Beckman DU530 spectrophotometer. Sterile TYP media was used as a blank. Inclusion bodies were purified as described (Gao, et al, *Prot. Sci.*7: 1245-49 (1998)). Cells were lysed by incubation for 30 minutes at room temperature in 'Lysis Buffer' (10 mM EDTA (from 0.5 M stock pH 8.0), 2 mM DTT (from 1 M stock in 10 mM sodium acetate pH 5.2, stored at −20° C.), 10 mM Tris pH 8.1 (from 2 M stock pH 8.1), 150 mM NaCl (from 4 M stock), 200 µg/ml lysozyme (from 20 mg/ml stock stored at −20° C.), 10% glycerol (from fluid), 2500 units of DNAase I and 10 mM MgCl₂ using a 50 ml Dounce homogeniser DNase I and lysozyme were from Sigma). Sonication, in lysis buffer, to break open the cells was performed using a 12 mM probe sonicator (Milsonix XL2020). The probe was tuned according to the manufacturers instructions. The resulting suspension was then diluted 1:1 in 'Triton Buffer' (0.5% (w/v) Triton X-100 (from fluid), 50 mM Tris pH 8.1 (from 2 M stock), 100 mM NaCl (from 5 M stock), 0.1% sodium azide (from solid), 10 mM EDTA (from 0.5 M stock pH 8.0), 2 mM DTT (from 1 M stock in 10 mM sodium acetate pH 5.2, stored at −20° C.), and left overnight. The inclusion bodies were separated from cell debris by centrifugation in a Beckman J2-21 centrifuge equipped with a JA-20 rotor as described (Gao, et al, *Prot. Sci.*7:1245-49 (1998)) and stored at −20° C. Inclusion bodies were then thawed and resuspended in 'Resuspension Buffer' (50 mM Tris pH 8.1 (from 2 M stock), 100 mM NaCl (from 4 M stock), 10 mM EDTA (from 0.5 M stock pH 8.0), 2 mM DTT (from 1 M stock in 10 mM sodium acetate pH 5.2, stored at −20° C.)), and denatured in 6M Guanidine and 10 mM DTT buffered with Tris-HCl pH 8.1 (all chemicals from Sigma).

The sCD8αα proteins were then refolded in vitro in the presence of 0.4M L-Arginine and purified by ion-exchange (PDKOS HS column) and/or gel filtration chromatography, for instance on a Pharmacia Superdex 75 column. The 99N→I and 99N→M sCD8αα mutants failed to refold correctly and therefore were not further assessed.

Example 13

Mammalian Expression Vectors Coding for Soluble CD8α

A. Native CD8α Lacking the Transmembrane Domain (Natural Splice Variant)

```
Primers:
Signal peptide forward primer      (SEQ ID NO:45)
5'-CCCCTCTAGA TGGCCTTACC AGTGACCGCC-3'

Cytoplasmic tail reverse primer    (SEQ ID NO:46)
5'-GGGGAATTCT TAGACGTATC TCGCCGAAAG GCT-3'
```

Using lymphocyte cDNA as template, PCRs is set up with primers at 0.5 µM each, dNTP at 0.2 mM each, and Pfu DNA polymerase at 0.05 U/µl in 1×Pfu buffer as provided from the supplier of the polymerase and run as follows: 10 minutes initial denaturation (94 C), followed by 20 cycles of denaturation (1 minute, 94 C); annealing (1 min, 55 C); elongation (3 minutes, 73 C); and a final elongation step for 10 minutes at 73 C.

Two dominant species are amplified, a full length product and a shorter product derived from a splice variant. This variant accounts for approximately 15% of the total CD8α mRNA in human CTLs. (Norment et al,. 1989, *J Immunol*, 142(9): 3312-9).

The short 615 base pair PCR fragment is purified and subcloned into the mammalian expression vector pcDNA3.1-(™ Invitrogen) between the XbaI and EcoRI restriction sites by standard techniques to give pEX119. In this plasmid, mammalian expression is controlled by a strong constitutive Cytomegalovirus (CMV) enhancer-promoter.

B. CD8-$\alpha_{S53}$ 1-120.

```
Primers:
Signal peptide forward primer      (SEQ ID NO:47)
5'-CCCCTCTAGA TGGCCTTACC AGTGACCGCC-3' aa. 120 reverse primer             (SEQ ID NO:48)
5'-GGGGAATTCT ATGGCGTCGT GGTGGG-3'
```

Using lymphocyte cDNA as template, PCR is set up with primers at 0.5 µM each, dNTP at 0.2 mM each, and Pfu DNA polymerase at 0.05 U/µl in 1×Pfu buffer as provided from the supplier of the polymerase and run as follows: 10 minutes initial denaturation (94 C), followed by 20 cycles of denaturation (1 minute, 94 C); annealing (1 min, 55 C); elongation (3 minutes, 73 C); a final elongation step for 10 minutes at 73 C.

The resulting 443 base pair PCR fragment is purified and subcloned into pcDNA3.1-(™ Invitrogen) between the XbaI and EcoRI restriction sites by standard techniques to give pEX120.

C. CD8-$\alpha_{N53}$ w/o Transmembrane Domain (Splice Variant)

pEX501 is made by PCR mutagenesis (in the same manner described in Example 1) using the primers shown and pEX119 as template. This plasmid codes for the natural CD8-α splice variant with a single point mutation Ser$_{53}$ Asn.

```
                                   (SEQ ID NO:49)
Amino Acid     Leu Leu Tyr Leu Asn Gln Asn Lys (SEQ ID NO:50)
Forward:   5'  CTC CTA TAC CTC AAC CAA AAC AAG CC (SEQ ID NO:51)
Reverse:   5'  GG CTT GTT TTG GTT GAG GTA TAG GAG
```

D. CD8-$\alpha_{N53}$ 1-120.

pEX502 is made by PCR mutagenesis (in the same manner described in Example 1) using the primers shown on pEX120. This plasmid codes for CD8-α amino acids −21 to 120 with a single point mutation Ser$_{53}$ Asn.

```
                                   (SEQ ID NO:52)
Amino Acid     Leu Leu Tyr Leu Asn Gln Asn Lys (SEQ ID NO:53)
Forward:   5'  CTC CTA TAC CTC AAC CAA AAC AAG CC (SEQ ID NO:54)
Reverse:   5'  GG CTT GTT TTG GTT GAG GTA TAG GAG
```

Example 14

Testing of WT and Ser$_{53}$→Asn Mutant sCD8αα Protein Binding to Tax and Flu HLA-A2/β2m Complexes sCD8αα Mutant proteins were prepared according to Example 12.

The refolding of the Tax and Flu HLA-A2/β2m complexes was carried out as described in (Gao, et al, *Prot. Sci.*7: 1245-49 (1998)) containing a tag sequence that can be enzymatically biotinylated (Schatz, *Biotechnology NY* 11: 1138-43 (1993); Altman, et al *Science* 274: 94-6 (1996); Wyer, et al. *Immunity* 10: 219-225 (1999)). The complexes were then biotinylated using the enzyme BirA (O'Callaghan, et al. *Anal Biochem* 266(1): 9-15 (1999)) to produce Tax and Flu HLA-A2/β2m complexes which were biotinylated towards the C-terminus of the HLA-A2 heavy chain. These protein complexes were immobilised on a streptavidin-modified BIAcore chip sensor cell in a BIAcore 3000 machine. The CD8 proteins were passed through the sensor cell at concentrations in the range of 0.025-11.5 mg/ml. The binding of WT and mutant sCD8αα to the Tax and Flu HLA-A2/β2m complexes was monitored by surface plasmon resonance (SPR).

Determination of the effects on HLA binding of mutations introduced in the sCD8αα protein was accomplished by passing sCD8αα protein through the BIAcore sensor cells and the levels of binding in these were compared. Any absent, or significant reduction, of mutant sCD8αα binding to peptide-HLA-A2/β2m complex observed, compared to that observed for WT sCD8aa, was concluded to demonstrate that the mutation introduced into the sCDαα protein had affected the ability of the protein to bind the HLA/β2m complex.

Both WT and mutant proteins were purified by gel filtration (Superdex 75HR 10/30) immediately prior to the binding experiments. Fractions containing protein pooled together and concentrated using a 10 kd cut-off Centriprep Kit (Millipore). The sCD8αα concentrations were measured using optical density at 280 nm wavelength (OD280) on a Beckman DU530 spectrophotometer. (measured in a capillary).

| sCD8aa WT: | Abs280 = 13.8 | (11.4 mg/ml) |
| sCD8aa 53S → N mutant: | Abs280 = 14 | (11.6 mg/ml) |

Chip utilised: CM-5 sensor chip.
Complexes Immobilised on the Chip:
  flowcell 1: Tax-HLA-A2
  flowcell 2: Tax-HLA-A2
  flowcell 3: Flu-HLA-A2
  flowcell 4: blank (no protein bound)
10 solutions of different CD8 (WT and mutant) concentrations were prepared and sent to all the flowcells.

Responses were recorded and plotted against CD8 concentration and the points were fitted in the following equation:

Response=$P1*[CD8]/(P2+[CD8])$

Where P1 is the calculated response that would occur when all HLA/β2m complexes were bound to CD8 and P2 is the Kd in μM.

The results are shown in FIGS. 2 and 3. The affinity of sCD8αα mutant $Ser_{53} \rightarrow Asn$ for the HLA-A2/β2m complexes (both Flu and Tax) is between 3 and 4 times higher than that of WT sCD8αα.

Example 15

Testing of Other Mutant sCD8αα Proteins Binding to Tax HLA-A2/β2m Complexes

The following sCD8αα mutants were expressed and refolded as described in Example 12.

| Mutant | Plasmid |
|---|---|
| $Gln_2 \rightarrow Lys$ | pEX 106 |
| $Asn_{28} \rightarrow Gln$ | pEX 107 |
| $Phe_{48} \rightarrow Glu$ | pEX 108 |
| $Leu_{97} \rightarrow Tyr$ | pEX 109 |
| $Leu_{97} \rightarrow Gln$ | pEX 110 |
| $Leu_{97} \rightarrow Ser$ | pEX 111 |

The ability of these mutants to bind Tax HLA-A2/β2m complexes was tested as described in Example 14.
The results obtained are as follows (see also FIG. 4):

| Mutant | Kd (μM) |
|---|---|
| $Gln_2 \rightarrow Lys$ | 363 |
| $Asn_{28} \rightarrow Gln$ | no binding* |
| $Phe_{48} \rightarrow Glu$ | no binding* |
| $Leu_{97} \rightarrow Tyr$ | 630 |
| $Leu_{97} \rightarrow Gln$ | no binding* |
| $Leu_{97} \rightarrow Ser$ | no binding* |

*No binding - response generated was too low to determine a Kd

None of the mutants assessed in this example produced a sCD8αα molecule with high binding affinity for Tax HLA-A2.

Example 16

Method for Assessing the Ability of Mutant Soluble CD8αα to Inhibit T Cell Activation Target cells are grown in RPMI culture medium containing 10% human serum for 5 days. These cells are incubated in RMPI medium containing 1 μM peptide for 2 hours. The target cells are placed into microtitre plates with CTL (cytotoxic T lymphocytes) at a range of Effector: Target cell (E:T) ratios. Supernatants are harvested after 2-16 hours.

Example combinations of Class I HLA molecules and their respective T cells:

| HLA | T cell Clone | Reference |
|---|---|---|
| A*0201 | AL1.1 | Salter et al, 1990 |
| B*08 | IM6/LC13 | Argaet et al, 1994 |

Experimental Design
Negative Control—Antigen presenting target cells
Positive Control—Antigen presenting target cells incubated in the presence of a range (0-100 μg/ml soluble WT CD8αα.
Test Samples—Antigen presenting target cells incubated in the presence of a range (0-100 μg/ml soluble mutant CD8αα.
Assay components for these experiments are:
  18 μl 10× peptide ($10^{-5}$ M)
  18 μl PBS (−ve control), or PBS with WT soluble CD8αα (+ve control), or PBS with mutant soluble CD8αα (test samples)
  50 μl APC Target Cells (5,000 cells)
  100 μl containing 5,000-50,000 CTL.

A standard cytokine assay, for example a macrophage inflammatory protein-1β (MIP-1β) assay (Quantikine®—Human M1β Immunoassay, Cat No: DMB00, R&D Systems Europe, Abingdon UK) is the carried out on the supernatant in accordance with the manufacturers instructions.

Alternative assays based on the cytokines IFN-γ and RANTES could also be used.

Chemokines are cell activation markers expressed by a range of cells including CTL. Therefore, any decrease in cytokine production observed from the Test samples compared the Controls indicates a reduction in T cell activation.

Example 17

Method for Assessing the Ability of Mutant Soluble CD8 to Inhibit T Cell Activation Target cells are grown in RPMI culture medium containing 10% human serum for 5 days. These cells are incubated in RMPI medium containing 1 μM peptide for 2 hours. The target cells are placed into microtitre plates with CTL (cytotoxic lymphocytes) at a range of Effector:Target cell (E:T) ratios. Supernatants are harvested after 2-16 hours.

Example combinations of Class I HLA molecules and their respective T cells:

| HLA | T cell Clone | Reference |
|---|---|---|
| A*0201 | AL1.1 | Salter et al, 1990 |
| B*08 | IM6/LC13 | Argaet et al, 1994 |

Experimental Design

Control—Non-transformed antigen presenting target cells

Test Samples—Antigen presenting target cells transformed to express mutant soluble CD8.

A standard cytokine assay, for example a macrophage inflammatory protein-1β (MIP-1β) assay (Quantikine® Human MIP-1≠ Immunoassay, Cat No: DMB00, R&D Systems Europe, Abingdon UK) is the carried out on the supernatant in accordance with the manufacturers instructions.

Alternative assays based on the cytokines IFN-γ and RANTES could also be used.

Chemokines are cell activation markers expressed by a range of cells including CTL. Therefore, any decrease in cytokine production observed from the Test samples compared the controls indicates a reduction in T cell activation.

Example 18

Test for Immunogenicity of Mutant β-2-microglobulin

Mutant soluble CD8αα molecules could potentially induce an immune response either by antibodies and/or T cells. The introduction of mutation(s) in the CD8αα protein could potentially introduce a conformational change in the protein structure, which would be recognised by antibodies as a structural foreign antigen or, alternatively, enzymatic degradation of mutant soluble CD8αα could produce peptides not normally presented by self MHC molecules. These mutant peptides would then be recognised as foreign and induce a cellular immune response. Therefore, mutants are tested in a transgenic rat model expressing human MHC class I molecule (HLA-B27 heavy chain+β-2-microglobulin) as follows.

1. Inject transgenic rats with 3-4 mg mutant soluble CD8αα.
2. Collect serum from rats after 21 days.
3. Analyse serum for the production of anti-mutant soluble CD8αα antibodies by an ELISA.

The procedure for this ELISA is: a. Bind mutant soluble CD8αα to bottom of well; b. Add serum from transgenic rat, which has been treated with mutant soluble CD8αα; c. wash three times with 200 μL of wash buffer; d. add the appropriate concentration of conjugated anti-rat antibody; e. wash three times with 200 μL of wash buffer; f. add 100 μL detection reagent (Alkaline Phosphatase, substrate pNPP) and read absorbance at 405 nm. Absorbance readings above negative control readings will indicate, that anti-mutant soluble CD8αα antibodies are present in the serum.

---

The invention claimed is:

1. A modified human CD8 αα molecule whose binding to MHC is enhanced compared to wild type CD8, wherein (a) each α chain of the molecule comprises SEQ ID NO:4 or (b) each α chain of the molecule comprises SEQ ID NO:4 except that Ala or Ser is substituted for $Cys_{33}$.

2. A molecule as claimed in claim 1, which is a soluble form of the modified CD8.

3. A molecule as claimed in claim 2, wherein $Cys_{33}$ of each CD8α chain thereof is mutated to Ala or Ser.

4. A multimer of a molecule as claimed in claim 1.

5. A composition comprising a modified CD8 molecule as defined in claim 1, together with a pharmaceutically acceptable diluent, excipient or carrier.

6. A dimer molecule as claimed in claim 1, wherein each α chain of the dimer molecule comprises SEQ ID NO:4.

* * * * *

SEQUENCE LISTING

```
<160> NUMBER OF SEQ ID NOS: 54

<210> SEQ ID NO 1
<211> LENGTH: 8
<212> TYPE: PRT
<213> ORGANISM: Homo sapiens
<220> FEATURE:
<223> OTHER INFORMATION: primer

<400> SEQUENCE: 1

Cys Ser Ser His Asn Lys Pro Cys
1               5

<210> SEQ ID NO 2
<211> LENGTH: 233
<212> TYPE: PRT
<213> ORGANISM: Homo sapiens
<220> FEATURE:
<223> OTHER INFORMATION: primer

<400> SEQUENCE: 2

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Asp Thr Phe Leu Leu Tyr Leu Ser Gln Asn Lys Pro Lys Ala Ala Glu
65                  70                  75                  80

Gly Leu Asp Thr Gln Arg Phe Ser Gly Lys Arg Leu Gly Asp Thr Phe
            85                  90                  95

Val Leu Thr Leu Ser Asp Phe Arg Arg Glu Asn Glu Gly Tyr Tyr Phe
            100                 105                 110

Cys Ser Ala Leu Ser Asn Ser Ile Met Tyr Phe Ser His Phe Val Pro
```

-continued

```
            115                 120                 125
Val Phe Leu Pro Ala Lys Pro Thr Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Ile Tyr Ile Trp Ala Pro Leu Ala Gly Thr Cys Gly
                180                 185                 190

Val Leu Leu Leu Ser Leu Val Ile Thr Leu Tyr Cys Asn His Arg Asn
                195                 200                 205

Arg Arg Arg Val Cys Lys Cys Pro Arg Pro Val Val Lys Ser Gly Asp
    210                 215                 220

Lys Pro Ser Leu Ser Ala Arg Tyr Val
225                 230
```

<210> SEQ ID NO 3
<211> LENGTH: 708
<212> TYPE: DNA
<213> ORGANISM: Homo sapiens
<220> FEATURE:
<223> OTHER INFORMATION: primer

<400> SEQUENCE: 3

```
atggcctrac cagtgaccgc cttgctcctg ccgctggcct tgctgctcca cgccgccagg      60
ccgagccagt tccgggtgtc gccgctggat cggacctgga actgggcga gacagtggag     120
ctgaagtgcc aggtgctgct gtccaacccg acgtcgggct gctcgtggct cttccagccg    180
cgcggcgccg ccgccagtcc caccttcctc ctatacctct cccaaaacaa gcccaaggcg    240
gccgaggggc tggacaccca gcggttctcg ggcaagaggt tggggacac cttcgtcctc    300
accctgagcg acttccgccg agagaacgag ggctactatt tctgctcggc cctgagcaac    360
tccatcatgt acttcagcca cttcgtgccg gtcttcctgc cagcgaagcc caccacgacg    420
ccagcgccgc gaccaccaac accggcgccc accatcgcgt cgcagcccct gtccctgcgc    480
ccagaggcgt gccggccagc ggcgggggc gcagtgcaca cgagggggct ggacttcgcc    540
tgtgatatct acatctgggc gcccttggcc gggacttgtg gggtccttct cctgtcactg    600
gttatcaccc tttactgcaa ccacaggaac cgaagacgtg tttgcaaatg tccccggcct    660
gtggtcaaat cgggagacaa gcccagcctt tcggcgagat acgtctaa                708
```

<210> SEQ ID NO 4
<211> LENGTH: 118
<212> TYPE: PRT
<213> ORGANISM: Homo sapiens
<220> FEATURE:
<223> OTHER INFORMATION: primer

<400> SEQUENCE: 4

```
Ser Gln Phe Arg Val Ser Pro Leu Asp Arg Thr Trp Asn Leu Gly Glu
  1               5                  10                  15

Thr Val Glu Leu Lys Cys Gln Val Leu Leu Ser Asn Pro Thr Ser Gly
                 20                  25                  30

Cys Ser Trp Leu Phe Gln Pro Arg Gly Ala Ala Asp Thr Phe Leu Leu
             35                  40                  45

Tyr Leu Asn Gln Asn Lys Pro Lys Ala Ala Glu Gly Leu Asp Thr Gln
         50                  55                  60
```

```
Arg Phe Ser Gly Lys Arg Leu Gly Asp Thr Phe Val Leu Thr Leu Ser
 65                  70                  75                  80

Asp Phe Arg Arg Glu Asn Glu Gly Tyr Tyr Phe Cys Ser Ala Leu Ser
                 85                  90                  95

Asn Ser Ile Met Tyr Phe Ser His Phe Val Pro Val Phe Leu Pro Ala
            100                 105                 110

Lys Pro Thr Thr Thr Pro
            115
```

<210> SEQ ID NO 5
<211> LENGTH: 363
<212> TYPE: DNA
<213> ORGANISM: Homo sapiens
<220> FEATURE:
<223> OTHER INFORMATION: primer

<400> SEQUENCE: 5

```
agtcaatttc gtgtatcacc gctggatcgg acctggaacc tgggcgagac agtggagctg      60
aagtgccagg tgctgctgtc caacccgacg tcgggctgct cgtggctctt ccagccgcgc     120
ggcgccgccg ccagtcccac cttcctccta tacctcaacc aaaacaagcc caaggcggcc     180
gaggggctgg acacccagcg gttctcgggc aagaggttgg gggacacctt cgtcctcacc     240
ctgagcgact ccgccgaga gaacgagggc tactatttct gctcggccct gagcaactcc      300
atcatgtact tcagccactt cgtgccggtc ttcctgccag cgaagcccac cacgacgcca     360
tag                                                                   363
```

<210> SEQ ID NO 6
<211> LENGTH: 233
<212> TYPE: PRT
<213> ORGANISM: Homo sapiens
<220> FEATURE:
<223> OTHER INFORMATION: primer

<400> SEQUENCE: 6

```
Met Ala Leu Pro Val Thr Ala Leu Leu Leu Pro Leu Ala Leu Leu Leu
 1               5                  10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
    50                  55                  60

Asp Thr Phe Leu Leu Tyr Leu Asn Gln Asn Lys Pro Lys Ala Ala Glu
 65                  70                  75                  80

Gly Leu Asp Thr Gln Arg Phe Ser Gly Lys Arg Leu Gly Asp Thr Phe
                 85                  90                  95

Val Leu Thr Leu Ser Asp Phe Arg Arg Glu Asn Glu Gly Tyr Tyr Phe
            100                 105                 110

Cys Ser Ala Leu Ser Asn Ser Ile Met Tyr Phe Ser His Phe Val Pro
        115                 120                 125

Val Phe Leu Pro Ala Lys Pro Thr Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175
```

```
Phe Ala Cys Asp Ile Tyr Ile Trp Ala Pro Leu Ala Gly Thr Cys Gly
            180                 185                 190

Val Leu Leu Leu Ser Leu Val Ile Thr Leu Tyr Cys Asn His Arg Asn
        195                 200                 205

Arg Arg Arg Val Cys Lys Cys Pro Arg Pro Val Val Lys Ser Gly Asp
    210                 215                 220

Lys Pro Ser Leu Ser Ala Arg Tyr Val
225                 230
```

<210> SEQ ID NO 7
<211> LENGTH: 708
<212> TYPE: DNA
<213> ORGANISM: Homo sapiens
<220> FEATURE:
<223> OTHER INFORMATION: primer

<400> SEQUENCE: 7

```
atggccttac cagtgaccgc cttgctcctg ccgctggcct tgctgctcca cgccgccagg      60
ccgagccagt tccgggtgtc gccgctggat cggacctgga acctgggcga cagtggag      120
ctgaagtgcc aggtgctgct gtccaacccg acgtcgggct gctcgtggct cttccagccg    180
cgcggcgccg ccgccagtcc caccttcctc ctatacctca ccaaaacaa gcccaaggcg     240
gccgagggc tggacaccca gcggttctcg ggcaagaggt tggggacac cttcgtcctc     300
accctgagcg acttccgccg agagaacgag ggctactatt tctgctcggc cctgagcaac    360
tccatcatgt acttcagcca cttcgtgccg gtcttcctgc agcgaagcc accacgacg     420
ccagcgccgc gaccaccaac accggcgccc accatcgcgt cgcagcccct gtccctgcgc    480
ccagaggcgt gccggccagc ggcgggggc gcagtgcaca cgagggggct ggacttcgcc    540
tgtgatatct acatctgggc gcccttggcc gggacttgtg gggtccttct cctgtcactg    600
gttatcaccc tttactgcaa ccacaggaac cgaagacgtg tttgcaaatg tccccggcct    660
gtggtcaaat cgggagacaa gcccagcctt tcggcgagat acgtctaa                  708
```

<210> SEQ ID NO 8
<211> LENGTH: 115
<212> TYPE: PRT
<213> ORGANISM: Homo sapiens
<220> FEATURE:
<223> OTHER INFORMATION: primer

<400> SEQUENCE: 8

```
Leu Gln Gln Thr Pro Ala Tyr Ile Lys Val Gln Thr Asn Lys Met Val
  1               5                  10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Val
    50                  55                  60

Glu Gln Glu Lys Ile Ala Val Phe Arg Asp Ala Ser Arg Phe Ile Leu
 65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp
115
```

-continued

<210> SEQ ID NO 9
<211> LENGTH: 348
<212> TYPE: DNA
<213> ORGANISM: Homo sapiens
<220> FEATURE:
<223> OTHER INFORMATION: primer

<400> SEQUENCE: 9
ctccagcaga cccctgcata cataaaggtg caaaccaaca agatggtgat gctgtcctgc      60
gaggctaaaa tctccctcag taacatgcgc atctactggc tgagacagcg ccaggcaccg     120
agcagtgaca gtcaccacga gttcctggcc ctctgggatt ccgcaaaagg gactatccac     180
ggtgaagagg tggaacagga gaagatagct gtgtttcggg atgcaagccg gttcattctc     240
aatctcacaa gcgtgaagcc ggaagacagt ggcatctact tctgcatgat cgtcgggagc     300
cccgagctga ccttcgggaa gggaactcag ctgagtgtgg ttgattaa                  348

<210> SEQ ID NO 10
<211> LENGTH: 8
<212> TYPE: PRT
<213> ORGANISM: Artificial Sequence
<220> FEATURE:
<223> OTHER INFORMATION: artificial peptide

<400> SEQUENCE: 10

Ala Pro Arg Pro Pro Thr Pro Ala
 1               5

<210> SEQ ID NO 11
<211> LENGTH: 8
<212> TYPE: PRT
<213> ORGANISM: Artificial Sequence
<220> FEATURE:
<223> OTHER INFORMATION: artificial peptide

<400> SEQUENCE: 11

Leu Leu Leu His Ala Ala Arg Pro
 1               5

<210> SEQ ID NO 12
<211> LENGTH: 8
<212> TYPE: PRT
<213> ORGANISM: Artificial Sequence
<220> FEATURE:
<223> OTHER INFORMATION: mutant peptide

<400> SEQUENCE: 12

Leu Leu Tyr Leu Asn Gln Asn Lys
 1               5

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
ctcctatacc tcaaccaaaa caagcc                                           26

<210> SEQ ID NO 14
<211> LENGTH: 26
<212> TYPE: DNA
<213> ORGANISM: Artificial Sequence

```
<220> FEATURE:
<223> OTHER INFORMATION: primer

<400> SEQUENCE: 14
ggcttgtttt ggttgaggta taggag                                              26

<210> SEQ ID NO 15
<211> LENGTH: 9
<212> TYPE: PRT
<213> ORGANISM: Artificial Sequence
<220> FEATURE:
<223> OTHER INFORMATION: mutant peptide

<400> SEQUENCE: 15

Asp Ile His Met Ser Lys Phe Arg Val
 1               5

<210> SEQ ID NO 16
<211> LENGTH: 29
<212> TYPE: DNA
<213> ORGANISM: Artificial Sequence
<220> FEATURE:
<223> OTHER INFORMATION: primer

<400> SEQUENCE: 16
gatatacata tgagtaaatt tcgtgtatc                                           29

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
gatacacgaa atttactcat atgtatatc                                           29

<210> SEQ ID NO 18
<211> LENGTH: 7
<212> TYPE: PRT
<213> ORGANISM: Artificial Sequence
<220> FEATURE:
<223> OTHER INFORMATION: mutant peptide

<400> SEQUENCE: 18

Leu Leu Ser Gln Pro Thr Ser
 1               5

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
gctgctgtcc cagccgacgt cgg                                                 23

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
```
ccgacgtcgg ctgggacagc agc                                              23

<210> SEQ ID NO 21
<211> LENGTH: 7
<212> TYPE: PRT
<213> ORGANISM: Artificial Sequence
<220> FEATURE:
<223> OTHER INFORMATION: mutant peptide

<400> SEQUENCE: 21

Ser Pro Thr Glu Leu Leu Tyr
 1               5

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
ccagtcccac cgaactccta tacc                                             24

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
ggtataggag ttcggtggga ctgg                                             24

<210> SEQ ID NO 24
<211> LENGTH: 7
<212> TYPE: PRT
<213> ORGANISM: Artificial Sequence
<220> FEATURE:
<223> OTHER INFORMATION: mutant peptide

<400> SEQUENCE: 24

Cys Ser Ala Tyr Ser Asn Ser
 1               5

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
tctgctcggc ctatagcaac tcca                                             24

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
tggagttgct ataggccgag caga                                             24

<210> SEQ ID NO 27
<211> LENGTH: 7

```
<212> TYPE: PRT
<213> ORGANISM: Artificial Sequence
<220> FEATURE:
<223> OTHER INFORMATION: mutant peptide

<400> SEQUENCE: 27

Cys Ser Ala Gln Ser Asn Ser
 1               5

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
ctgctcggcc cagagcaact cc                                              22

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
ggagttgctc tgggccgagc ag                                              22

<210> SEQ ID NO 30
<211> LENGTH: 7
<212> TYPE: PRT
<213> ORGANISM: Artificial Sequence
<220> FEATURE:
<223> OTHER INFORMATION: mutant peptide

<400> SEQUENCE: 30

Cys Ser Ala Ser Ser Asn Ser
 1               5

<210> SEQ ID NO 31
<211> LENGTH: 23
<212> TYPE: DNA
<213> ORGANISM: Artificial Sequence
<220> FEATURE:
<223> OTHER INFORMATION: primer

<400> SEQUENCE: 31
ctgctcggcc tcgagcaact cca                                             23

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
tggagttgct cgaggccgag cag                                             23

<210> SEQ ID NO 33
<211> LENGTH: 7
<212> TYPE: PRT
<213> ORGANISM: Artificial Sequence
<220> FEATURE:
<223> OTHER INFORMATION: mutant peptide
```

<400> SEQUENCE: 33

Ala Leu Ser Ile Ser Ile Met
1               5

<210> SEQ ID NO 34
<211> LENGTH: 24
<212> TYPE: DNA
<213> ORGANISM: Artificial Sequence
<220> FEATURE:
<223> OTHER INFORMATION: primer

<400> SEQUENCE: 34
cggccctgag catctccatc atgt                                          24

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
acatgatgga gatgctcagg gccg                                          24

<210> SEQ ID NO 36
<211> LENGTH: 7
<212> TYPE: PRT
<213> ORGANISM: Artificial Sequence
<220> FEATURE:
<223> OTHER INFORMATION: mutant peptide

<400> SEQUENCE: 36

Ala Leu Ser Met Ser Ile Met
1               5

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
ggccctgagc atgtccatca tgta                                          24

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
tacatgatgg acatgctcag ggcc                                          24

<210> SEQ ID NO 39
<211> LENGTH: 7
<212> TYPE: PRT
<213> ORGANISM: Artificial Sequence
<220> FEATURE:
<223> OTHER INFORMATION: mutant peptide

<400> SEQUENCE: 39

Thr Ser Gly Ala Ser Trp Leu
1               5

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
gacgtcgggc gcctcgtggc tc                                              22

<210> SEQ ID NO 41
<211> LENGTH: 22
<212> TYPE: DNA
<213> ORGANISM: Artificial Sequence
<220> FEATURE:
<223> OTHER INFORMATION: primer

<400> SEQUENCE: 41
gagccacgag gcgcccgacg tc                                              22

<210> SEQ ID NO 42
<211> LENGTH: 7
<212> TYPE: PRT
<213> ORGANISM: Artificial Sequence
<220> FEATURE:
<223> OTHER INFORMATION: mutant peptide

<400> SEQUENCE: 42

Thr Ser Gly Ser Ser Trp Leu
 1               5

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
gacgtcgggc agctcgtggc tc                                              22

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
gagccacgag ctgcccgacg tc                                              22

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
cccctctaga tggccttacc agtgaccgcc                                      30

<210> SEQ ID NO 46
<211> LENGTH: 33
<212> TYPE: DNA
<213> ORGANISM: Artificial Sequence
<220> FEATURE:

```
<223> OTHER INFORMATION: primer

<400> SEQUENCE: 46 gggaattct tagacgtatc tcgccgaaag gct                                33

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
cccctctaga tggccttacc agtgaccgcc                                   30

<210> SEQ ID NO 48
<211> LENGTH: 26
<212> TYPE: DNA
<213> ORGANISM: Artificial Sequence
<220> FEATURE:
<223> OTHER INFORMATION: primer

<400> SEQUENCE: 48
ggggaattct atggcgtcgt ggtggg                                       26

<210> SEQ ID NO 49
<211> LENGTH: 8
<212> TYPE: PRT
<213> ORGANISM: Artificial Sequence
<220> FEATURE:
<223> OTHER INFORMATION: mutant peptide

<400> SEQUENCE: 49

Leu Leu Tyr Leu Asn Gln Asn Lys
 1               5

<210> SEQ ID NO 50
<211> LENGTH: 26
<212> TYPE: DNA
<213> ORGANISM: Artificial Sequence
<220> FEATURE:
<223> OTHER INFORMATION: primer

<400> SEQUENCE: 50
ctcctatacc tcaaccaaaa caagcc                                       26

<210> SEQ ID NO 51
<211> LENGTH: 26
<212> TYPE: DNA
<213> ORGANISM: Artificial Sequence
<220> FEATURE:
<223> OTHER INFORMATION: primer

<400> SEQUENCE: 51
ggcttgtttt ggttgaggta taggag                                       26

<210> SEQ ID NO 52
<211> LENGTH: 8
<212> TYPE: PRT
<213> ORGANISM: Artificial Sequence
<220> FEATURE:
<223> OTHER INFORMATION: mutant peptide

<400> SEQUENCE: 52

Leu Leu Tyr Leu Asn Gln Asn Lys
 1               5
```

```
<210> SEQ ID NO 53
<211> LENGTH: 26
<212> TYPE: DNA
<213> ORGANISM: Artificial Sequence
<220> FEATURE:
<223> OTHER INFORMATION: primer

<400> SEQUENCE: 53
ctcctatacc tcaaccaaaa caagcc                                          26

<210> SEQ ID NO 54
<211> LENGTH: 26
<212> TYPE: DNA
<213> ORGANISM: Artificial Sequence
<220> FEATURE:
<223> OTHER INFORMATION: primer

<400> SEQUENCE: 54
ggcttgtttt ggttgaggta taggag                                          26
```